United States Patent
Ueda

(10) Patent No.: US 11,329,744 B2
(45) Date of Patent: May 10, 2022

(54) SENSOR SYSTEM, TRANSMISSION TERMINAL, TIME INFORMATION PROCESSING DEVICE, AND SYNCHRONIZATION METHOD

(71) Applicant: KABUSHIKI KAISHA TOSHIBA, Tokyo (JP)

(72) Inventor: Yuki Ueda, Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 49 days.

(21) Appl. No.: 16/810,126

(22) Filed: Mar. 5, 2020

(65) Prior Publication Data

US 2021/0013981 A1    Jan. 14, 2021

(30) Foreign Application Priority Data

Jul. 9, 2019    (JP) .............................. JP2019-127718

(51) Int. Cl.
*H04J 3/06* (2006.01)
*H04L 29/08* (2006.01)
*H04L 67/12* (2022.01)

(52) U.S. Cl.
CPC ............ *H04J 3/0638* (2013.01); *H04L 67/12* (2013.01)

(58) Field of Classification Search
CPC .............................. H04J 3/0638; H04L 67/12
See application file for complete search history.

(56) References Cited

U.S. PATENT DOCUMENTS 8,504,864 B2 *   8/2013   Menon ................... H04L 12/403
                                                              713/401
8,892,031 B2 *   11/2014  Ben Hamida .......... H04B 17/40
                                                              455/13.1

(Continued)

FOREIGN PATENT DOCUMENTS

JP      2013-29340 A      2/2013
WO   WO 2018/151202 A1    8/2018

OTHER PUBLICATIONS

Maróti et al., "The Flooding Time Synchronization Protocol," Proceedings of the 2$^{nd}$ International Conference on Embedded Networked Sensor Systems, 11 pages (2004).

(Continued)

*Primary Examiner* — Christopher M Crutchfield
*Assistant Examiner* — Tito Q Pham
(74) *Attorney, Agent, or Firm* — Finnegan, Henderson, Farabow, Garrett & Dunner L.L.P.

(57) ABSTRACT

According to one embodiment, a transmission terminal, a time information processing device, and a synchronization method capable of improving synchronization accuracy in a wireless network are provided. According to an embodiment, a sensor system includes a sensor, a transmission terminal, and a time information processing device. The transmission terminal includes an event signal generator, an event time determiner, a communication time determiner, and a communicator. The event signal generator detects the occurrence of an event on the basis of a physical quantity detected by the sensor. The event time determiner determines a detection time of the event. The communication time determiner determines a transmission time at the time of transmission to the time information processing device. The communicator transmits time information to the time information processing device. The time information processing device includes a reception time determiner and a (Continued)

time information processor. The reception time determiner determines a reception time of the time information transmitted from the transmission terminal. The time information processor performs a process based on a plurality of transmission times and a plurality of reception times.

11 Claims, 15 Drawing Sheets

(56) References Cited

U.S. PATENT DOCUMENTS

| | | |
|---|---|---|
| 9,555,883 B1* | 1/2017 | Navot .................. G05D 1/0202 |
| 2004/0257242 A1* | 12/2004 | Bruemmer ............... H04Q 9/00 |
| | | 340/870.14 |
| 2005/0041692 A1* | 2/2005 | Kallstenius ........... H04J 3/0667 |
| | | 370/503 |

OTHER PUBLICATIONS

Kusý et al., "Elapsed time on arrival: a simple and versatile primitive for canonical time synchronization services," Int. J. Ad Hoc and Ubiquitous Computing, vol. 1, No. 4, p. 239-251 (2006).
Bouzid et al., "Structural Health Monitoring of Wind Turbine Blades: Acoustic Source Localization Using Wireless Sensor Networks," Hindawi Publishing Corporation, Journal of Sensors, 2015:139695, pp. 1-11 (Dec. 15, 2014).
Sommer et al., "Gradient Clock Synchronization in Wireless Sensor Networks," Proceedings of the 2009 International Conference on Information Processing in Sensor Networks, pp. 37-48 (2009).

* cited by examiner

SENSOR SYSTEM, TRANSMISSION TERMINAL, TIME INFORMATION PROCESSING DEVICE, AND SYNCHRONIZATION METHOD

CROSS-REFERENCE TO RELATED APPLICATION

This application is based upon and claims the benefit of priority from Japanese Patent Application No. 2019-127718, filed Jul. 9, 2019, the entire contents of which are incorporated herein by reference.

FIELD

Embodiments of the present invention relate to a sensor system, a transmission terminal, a time information processing device, and a synchronization method.

BACKGROUND

In recent years, various types of sensing data have been able to be collected due to power saving and price reduction of sensors and the development of networks. Thus, there is an active movement for utilizing sensing data. A method of utilizing sensing data is structural health monitoring. The structural health monitoring is technology for sensing physical quantities such as displacement, vibration, and pressure by means of sensors installed on structures such as bridges, and diagnosing damage and deterioration states of structures using various signal processing techniques. In such a monitoring system, not only single sensor information but also mutual information between a plurality of sensors is important and accurate time acquisition is required. Because the same clock can be used when a single terminal device and a sensor are connected using wires, little time error in the sensor information occurs. On the other hand, in the case of a system including a plurality of terminal devices using a wireless network, time synchronization is necessary because there are a plurality of clocks. As an example of such time synchronization, a method using a flooding time synchronization protocol (FTSP) in which a sensor and a server communicate with each other and a method using elapsed time on arrival (ETA) are known.

In the above-described method, two-way communication is necessary and the correction of a time on the sensor side is necessary, such that the reception power and the amount of processing of the sensor increase. In FTSP, in order to deliver the time of the server to the sensor side, it is necessary to perform reception periodically for accurate synchronization. In ETA, because the sensor only needs to transmit a difference between a sensing time and a transmission time to the server, this problem caused in FTSP can be solved.

However, when instability of a clock for generating a time, a transmission delay due to carrier sense or the like, and retransmission due to a packet error occur and a central processing unit (CPU) or the like is interrupted by another process, a process changes. Thus, synchronization accuracy may be reduced.

DETAILED DESCRIPTION

The present invention provides a problem to be solved by the present invention is to provide a sensor system, a transmission terminal, a time information processing device, and a synchronization method capable of improving synchronization accuracy in a wireless network.

According to one embodiment, a sensor system includes a sensor, a transmission terminal, and a time information processing device. The sensor detects a physical quantity. The transmission terminal is connected to the sensor. The time information processing device performs a process based on information transmitted from the transmission terminal. The transmission terminal includes an event signal generator, an event time determiner, a communication time determiner, and a communicator. The event signal generator detects the occurrence of an event on the basis of the physical quantity detected by the sensor. The event time determiner determines a detection time of the event. The communication time determiner determines a transmission time at the time of transmission to the time information processing device. The communicator transmits time information of the transmission time and time information of the detection time of the event to the time information processing device. The time information processing device includes a reception time determiner and a time information processor. The reception time determiner determines a reception time of the time information transmitted from the transmission terminal. The time information processor performs a process based on a plurality of transmission times and a plurality of reception times.

Hereinafter, a sensor system, a transmission terminal, a time information processing device, and a synchronization method according to embodiments will be described with reference to the drawings.

First Embodiment

Figure 1:
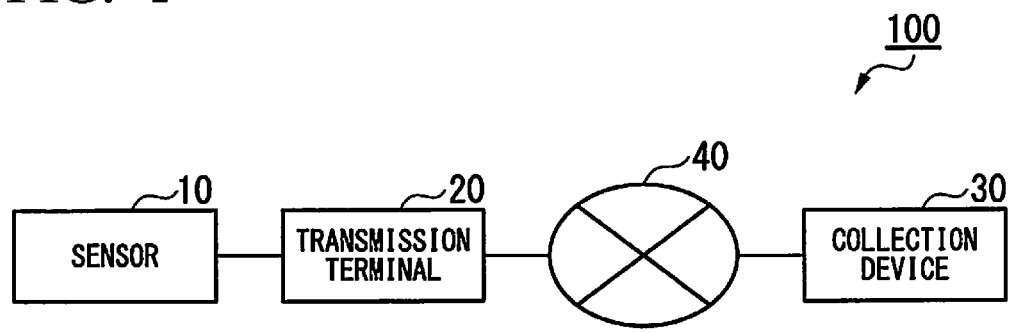
FIG. 1 is a diagram showing a system configuration of a sensor system according to a first embodiment.

FIG. 1 is a diagram showing a system configuration of a sensor system 100 according to a first embodiment. The sensor system 100 includes a sensor 10, a transmission terminal 20, and a collection device 30. The sensor 10 and the transmission terminal 20 are connected by a wire. The transmission terminal 20 and the collection device 30 are wirelessly connected via a network 40. The network 40 is, for example, a network of an industrial, scientific, and medical (ISM) band. The wireless connection between the transmission terminal 20 and the collection device 30 is not necessarily limited to a wireless LAN, and any communication scheme may be used as long as wireless communication is possible. Although a configuration in which the sensor system 100 includes a single sensor 10 and a single transmission terminal 20 is shown in FIG. 1, the sensor system 100 may include a plurality of sensors 10 and a plurality of transmission terminals 20.

The sensor 10 is a sensor configured to detect a physical quantity. The sensor 10 is, for example, an acoustic emission (AE) sensor, an acceleration sensor, a microphone, a temperature sensor, or the like. The sensor 10 may be another sensor as long as a physical quantity can be detected. The sensor 10 converts the detected physical quantity into an electrical signal. The sensor 10 transmits the electrical signal to the transmission terminal 20.

The transmission terminal 20 transmits transmission data including time information to the collection device 30. For example, the transmission terminal 20 detects an event on the basis of the electrical signal output from the sensor 10 and transmits transmission data including at least one or both of an occurrence time of the detected event (hereinafter referred to as "event detection time") and a transmission time to the collection device 30. Here, the event is an event that has occurred outside or inside the device. In the following embodiment, an event will be described as an example of an event that has occurred outside the device (for example, an event based on a detection result of a sensor). The transmission time is a time at which the transmission terminal 20 has transmitted transmission data including information of an event detection time to the collection device 30.

The collection device 30 collects the transmission data transmitted from the transmission terminal 20. The collection device 30 collects a plurality of transmission times and event detection times from one transmission terminal 20 for each sensor 10. The collection device 30 performs a process based on the collected transmission times, the collected event detection times, and reception times corresponding to the transmission times. The reception time corresponding to the transmission time is a time at which transmission data including information of the transmission time transmitted from the transmission terminal 20 has been received.

Figure 2:
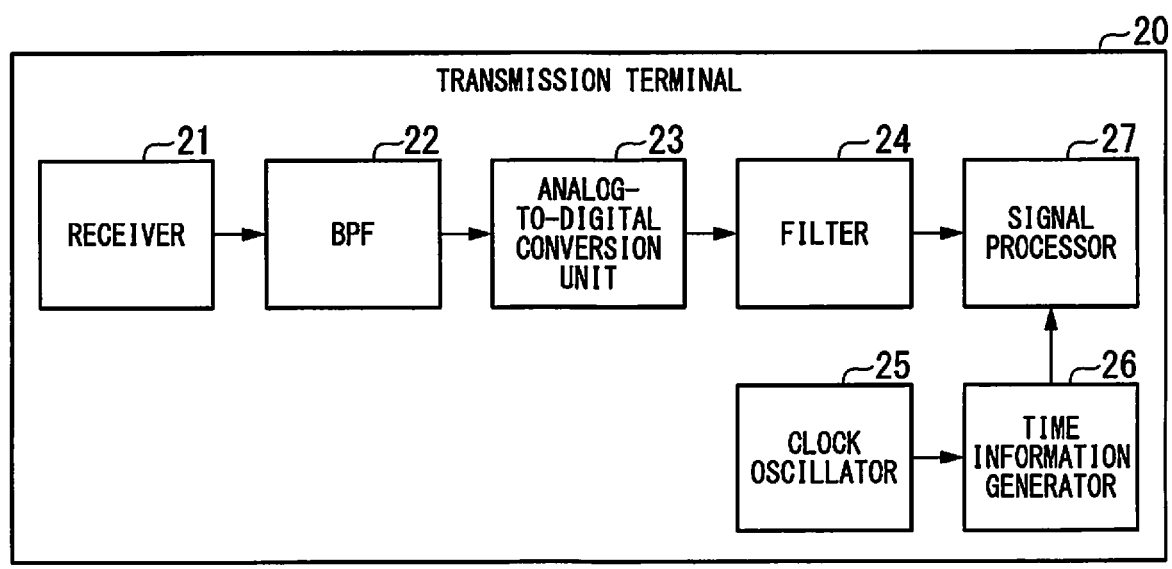
FIG. 2 is a schematic block diagram showing a function of a transmission terminal according to the first embodiment.

FIG. 2 is a schematic block diagram showing a function of the transmission terminal 20 according to the first embodiment.

The transmission terminal 20 includes a receiver 21, a BPF 22, an analog-to-digital conversion unit 23, a filter 24, a clock oscillator 25, a time information generator 26, and a signal processor 27.

The receiver 21 receives an electrical signal transmitted from the sensor 10. The receiver 21 outputs the received electrical signal to the BPF 22.

The BPF 22 removes noise from the electrical signal received by the receiver 21. The BPF 22 is a filter for removing noise. The BPF 22 outputs a noise-removed signal to the analog-to-digital conversion unit 23.

The analog-to-digital conversion unit 23 converts an analog signal into a digital signal by quantizing the noise-removed signal output from the BPF 22. The analog-to-digital conversion unit 23 outputs the digital signal to the filter 24.

The filter 24 removes noise from the digital signal output from the analog-to-digital conversion unit 23. The filter 24 is a filter for removing noise. The filter 24 outputs the noise-removed signal to the signal processor 27.

In the following description, a process performed by the receiver 21, the BPF 22, the analog-to-digital conversion unit 23, and the filter 24 will be described as preprocessing.

The clock oscillator 25 generates a clock signal. Specifically, the clock oscillator 25 determines a time width of 1 sec in the transmission terminal 20. The clock oscillator 25 is configured using, for example, a voltage variable crystal oscillator such as a voltage controlled xtal oscillator (VCXO). The clock oscillator 25 outputs a clock signal to the time information generator 26.

The time information generator 26 determines a time in the transmission terminal 20 in accordance with the clock signal output from the clock oscillator 25. For example, the time information generator 26 is a counter having a register. That is, the time information generator 26 counts the number of edges of the clock signal and stores a cumulative count value from the power-on time of the transmission terminal 20 as time information in the register.

The signal processor 27 determines an event detection time and a transmission time on the basis of a noise-removed digital signal output from the filter 24 and the time information generated by the time information generator 26. The event detection time may be, for example, the number of clocks, or may be hours:minutes:seconds.

Figure 3:
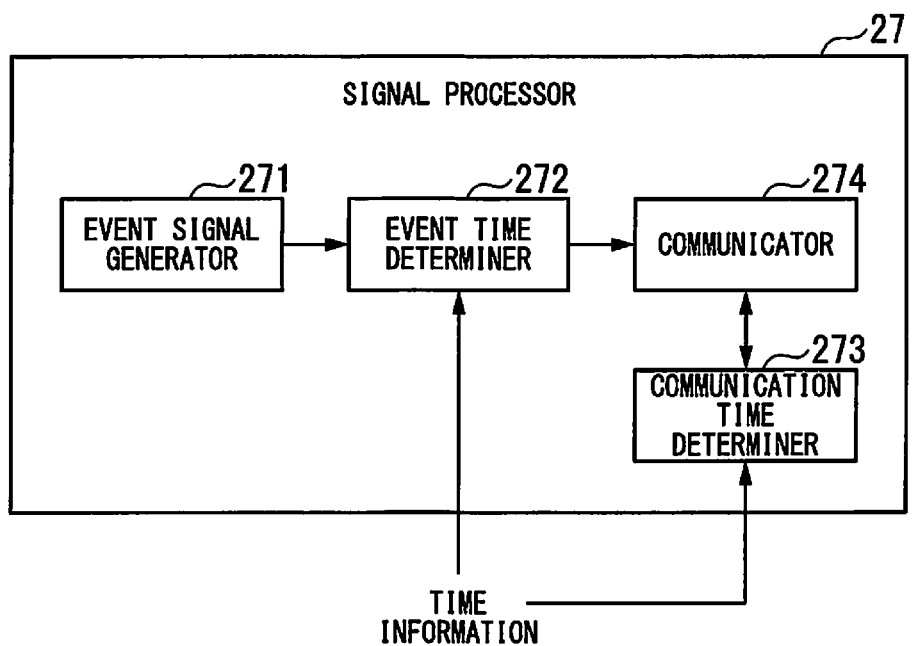
FIG. 3 is a schematic block diagram showing an internal configuration of a signal processor according to the first embodiment.

FIG. 3 is a schematic block diagram showing an internal configuration of the signal processor 27 according to the first embodiment. The signal processor 27 includes an event signal generator 271, an event time determiner 272, a communication time determiner 273, and a communicator 274.

The event signal generator 271 generates a gate signal indicating whether or not a waveform of a noise-removed digital signal is being sustained. The event signal generator 271 is implemented by, for example, an envelope detector and a comparator. The envelope detector detects the envelope of the noise-removed digital signal. The envelope is extracted by, for example, squaring the noise-removed digital signal and performing a predetermined process (for example, a process using a low-pass filter or a Hilbert transform) on the squared output value. The comparator determines whether or not the envelope of the noise-removed digital signal is greater than or equal to a predetermined threshold value.

The event signal generator 271 outputs a first gate signal indicating that the waveform of the noise-removed digital signal is being sustained to the event time determiner 272 when the envelope of the noise-removed digital signal is greater than or equal to a predetermined threshold value. When the first gate signal has been output, this indicates that an event has occurred. On the other hand, when the envelope of the noise-removed digital signal is less than the predetermined threshold value, the event signal generator 271 outputs a second gate signal indicating that the waveform of the noise-removed digital signal is not being sustained to the event time determiner 272. When the second gate signal has been output, this indicates that the event has ended. As a method of detecting event occurrence, ChangeFinder, Akaike's Information Criterion (AIC), or the like may be used.

The event time determiner 272 inputs either the first gate signal or the second gate signal output from the event signal generator 271 and the time information. The event time determiner 272 determines the event detection time on the basis of the input gate signal. Specifically, the event time determiner 272 determines a time when the envelope has been greater than or equal to a predetermined threshold value, i.e., a time when the first gate signal has been input as an event detection time.

The communication time determiner 273 inputs time information. The communication time determiner 273 monitors the communicator 274 and determines a transmission time. The communication time determiner 273 may cause the communicator 274 to perform wireless communication at a time provided through a notification by determining the transmission time before wireless transmission and notifying the communicator 274 of the transmission time. The transmission time generally indicates a start time, but is not limited thereto as long as it is single. For example, the communicator 274 may externally output a signal when transmission starts and the communication time determiner 273 may determine the transmission time according to the signal. The communication time determiner 273 may determine the transmission time during wireless transmission, may incorporate the transmission time in the transmission data transmitted by the communicator 274, and may cause the transmission time to be transmitted after the end of wireless transmission.

The communicator 274 is a communication interface that performs communication with the collection device 30 via the network 40. The communicator 274 transmits either or both of the generated event detection time and transmission time to the collection device 30 at a predetermined timing through wireless communication. The predetermined timing may be, for example, a timing when the time determined by the communication time determiner 273 has been reached or may be a timing when a predetermined period of time has elapsed after transmission was performed once. A radio frequency band for use in communication of the communicator 274 is, for example, a band such as 2.4 GHz or 920 MHz. The communicator 274 may include a storage unit. The storage unit has, for example, a dual port RAM and stores an event detection time and a transmission time. The storage unit is not necessarily provided in the communicator 274 and may be provided within the transmission terminal 20. The communicator 274 can also perform transmission at an appropriate timing so that the event detection time and the transmission time are transmitted together or the event detection time and the transmission time are transmitted separately.

Next, the hardware of the transmission terminal 20 will be described. The power of the transmission terminal 20 is supplied from an external power source, a primary battery, a secondary battery, a solar battery, an energy harvester, or the like. The transmission terminal 20 is implemented from an analog circuit and a digital circuit. The digital circuit is implemented by, for example, an FPGA or a microcomputer. The digital circuit may be implemented by a dedicated LSI. Also, the transmission terminal 20 may be equipped with a non-volatile memory such as a flash memory or a removable memory.

Figure 4:
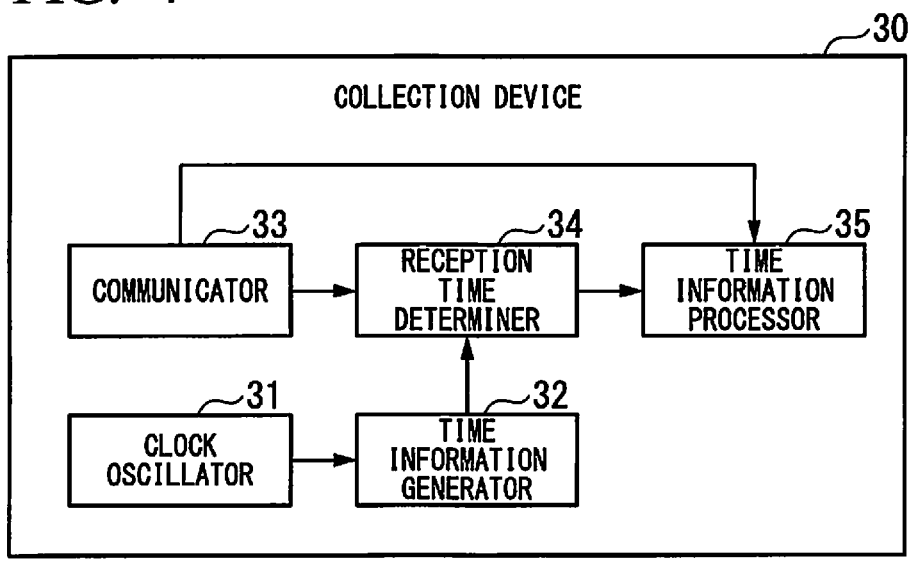
FIG. 4 is a schematic block diagram showing a function of a collection device according to the first embodiment.

FIG. 4 is a schematic block diagram showing a function of the collection device 30 according to the first embodiment.

The collection device 30 includes a central processing unit (CPU), a memory, an auxiliary storage device, and the like connected by a bus, and executes a collection program. By executing the collection program, the collection device 30 functions as a device including a clock oscillator 31, a time information generator 32, a communicator 33, a reception time determiner 34, and a time information processor 35. Also, all or some of functions of the collection device 30 may be implemented using hardware such as an application specific integrated circuit (ASIC), a programmable logic device (PLD), or a field programmable gate array (FPGA). Also, the collection program may be recorded on a computer-readable recording medium. The computer-readable recording medium is, for example, a flexible disk, a magneto-optical disk, a ROM, a portable medium such as a CD-ROM, or a storage device such as a hard disk built into the computer system. The collection program may be transmitted/received via a telecommunication circuit.

The clock oscillator 31 generates a clock signal. Specifically, the clock oscillator 31 determines a time width of 1 sec in the collection device 30. The clock oscillator 31 is configured using, for example, a voltage variable crystal oscillator such as a VCXO. The clock oscillator 31 outputs a clock signal to the time information generator 32.

The time information generator 32 determines a time in the collection device 30 according to the clock signal output from the clock oscillator 25. For example, the time information generator 32 is a counter having a register. That is, the time information generator 32 counts the number of edges of the clock signal and stores a cumulative count value from the power-on time of the collection device 30 as time information in the register.

The communicator 33 is a communication interface that performs communication with the transmission terminal 20 via the network 40. The communicator 33 receives information of the event detection time and the transmission time transmitted from the transmission terminal 20.

The reception time determiner 34 determines a reception time on the basis of a received signal. Specifically, the reception time determiner 34 determines a time at which the signal transmitted from the transmission terminal 20 has been received by the communicator 33 as the reception time.

The reception time generally indicates a reception start time, a time when a preamble has been discovered, or a synchronization word discovery time, but is not limited thereto.

The time information processor 35 estimates an event detection time when an event occurs by statistically processing a plurality of transmission times and a plurality of reception times that have been received. The time information processor 35 includes a storage unit that stores information of the transmission time and event detection time received by the communicator 33 and the estimated event detection time.

Figure 5:
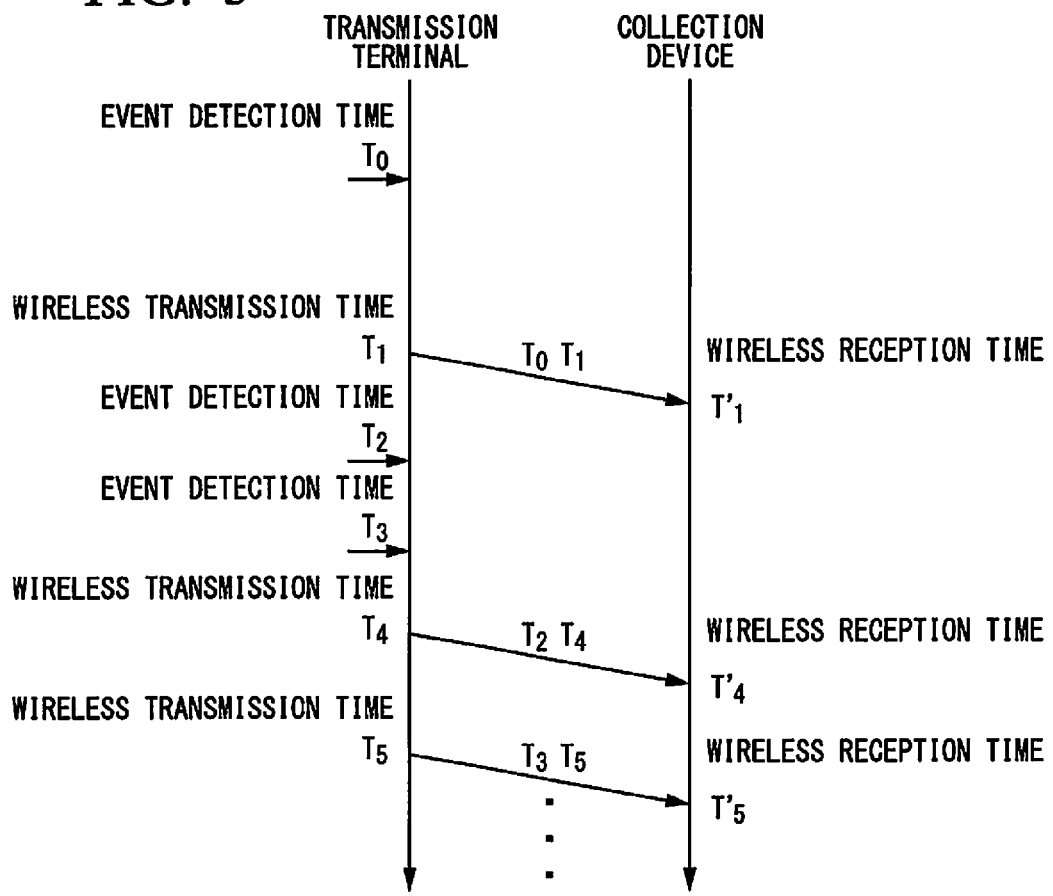
FIG. 5 is an explanatory diagram showing time processing according to the first embodiment.
Figure 6:
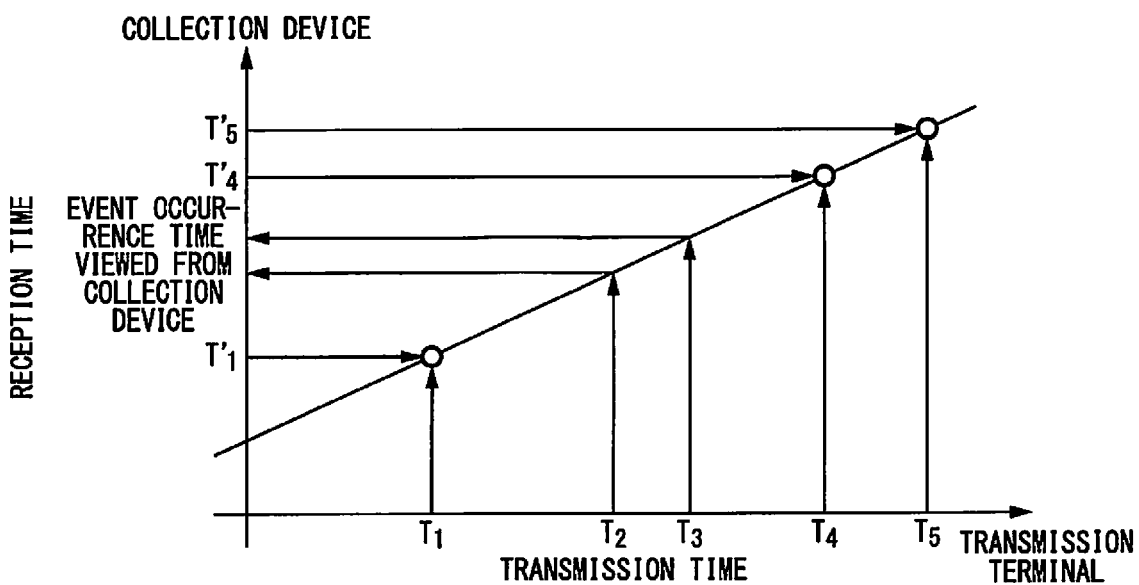
FIG. 6 is an explanatory diagram showing time processing according to the first embodiment.

FIGS. 5 and 6 are explanatory diagrams showing time processing according to the first embodiment.

As shown in FIG. 5, when an event occurs, the transmission terminal 20 acquires the event detection time by means of the event time determiner 272 and transmits information of the event detection time to the collection device 30 by means of the communicator 274. Specifically, when an event occurs, the transmission terminal 20 first determines a time $T_0$ when the event has occurred as the event detection time. Next, the transmission terminal 20 generates transmission data including the event detection time $T_0$ and a transmission time $T_1$ and transmits the generated transmission data to the collection device 30 at the time $T_1$. The collection device 30 receives the transmission data transmitted from the transmission terminal 20. The collection device 30 determines a time $T'_1$ when the transmission data has been received as a reception time. The collection device 30 determines the reception time in the reception time determiner 34 every time transmission data including at least the transmission time is received from the transmission terminal 20. As shown in FIG. 5, when an event occurs earlier than the transmission operation, transmission by the transmission terminal 20 is on standby and transmission is started at an available transmission timing.

FIG. 6 shows a relationship between a transmission time of the transmission terminal 20 and a reception time of the collection device 30. The collection device 30 obtains a graph shown in FIG. 6 on the basis of reception time information and transmission time information transmitted from the transmission terminal 20. For example, the collection device 30 can obtain a relationship related to times such as a transmission time $T_1$ and a reception time $T'_1$ and a transmission time $T_2$ and a reception time T'2. In the present embodiment, the collection device 30 statistically processes time stamps and counter values related to a plurality of pieces of transmission data, thereby acquiring a relationship between counter values and estimating an event detection time. The relationship between the counter values can be obtained by regression analysis and may be obtained in a scheme such as a least squares method or principal component analysis (PCA). In this case, the event detection time can be estimated from the relationship of y=ax+b. When the relationship between the counter values is obtained, a parametric or non-parametric method may be used. Also, it is not necessary to wait for all events to occur. If two or more transmission times and two or more reception times can be obtained between one transmission terminal 20 and the collection device 30, the event detection time can be estimated.

Also, the collection device 30 may calculate a time difference (for example, a difference $\Delta T_{32}$ between $T_3$ and $T_2$) obtained using a plurality of transmission times. In this case, the collection device 30 can convert the event detection time into necessary information without directly estimating the event detection time.

As compared with a case in which only a reception time stamp (a reception time) is used or a case in which an estimation scheme such as ETA in the conventional technology is used, clock-related errors and errors due to priority processing and the like in a microprocessor are averaged. Thus, an error of the event detection time can be reduced. Also, because the event detection time is converted into the counter value of the collection device 30 on the reception side, a comparison between a plurality of terminals is facilitated. Thus, it is extremely useful for application to an application with a high sampling rate such as position location by a sensor.

Figure 7:
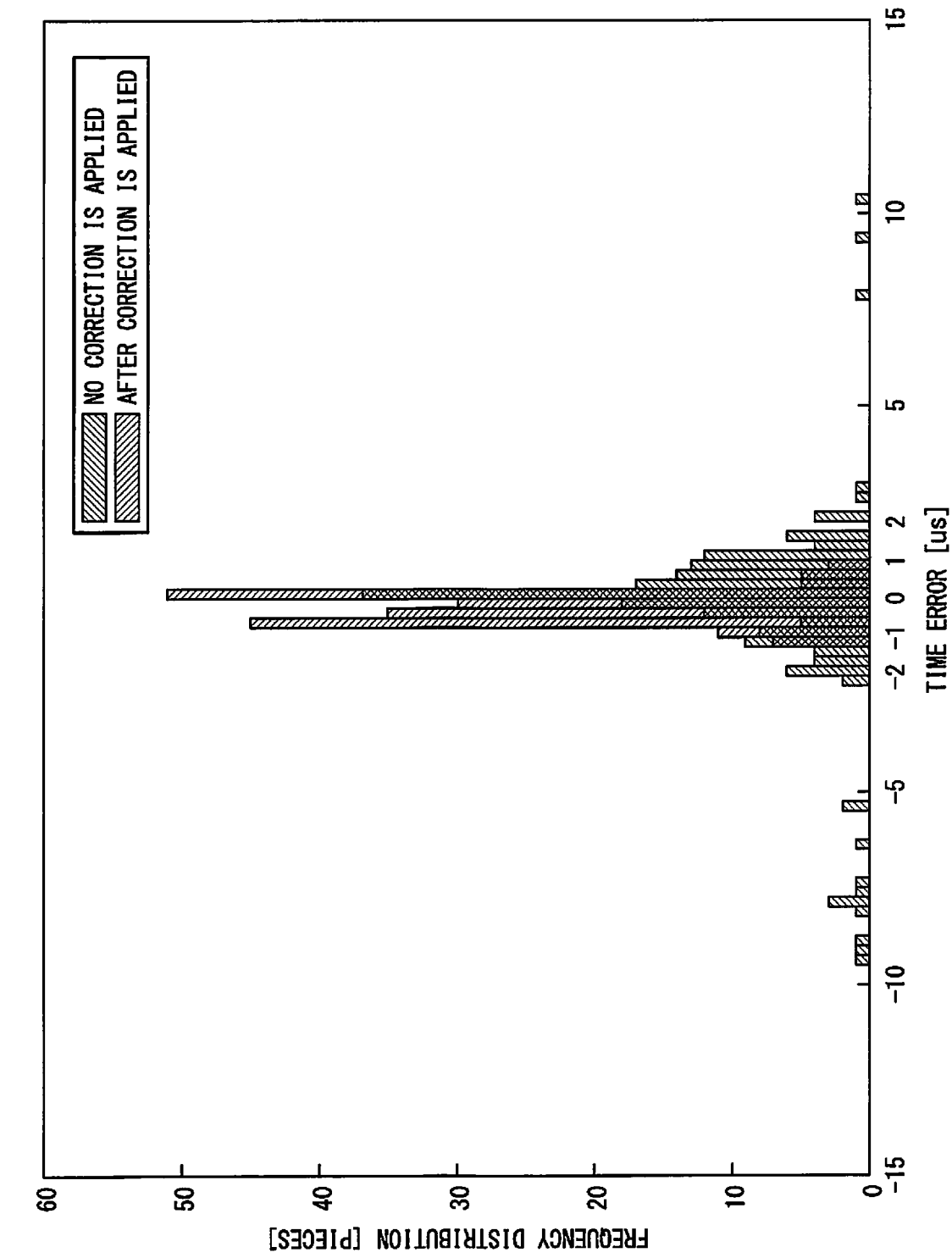
FIG. 7 is a diagram showing a result of comparison between conventional technology and technology according to the present embodiment.

FIG. 7 is a diagram showing a result of comparison between the conventional technology and the technology according to the present embodiment. In the graph shown in FIG. 7, the horizontal axis represents a time error, and the vertical axis represents a frequency distribution. In FIG. 7, a result of experimentally measuring the frequency distribution of the error of the event detection time estimated by the counter value of the collection device 30 when an event occurs simultaneously in a plurality of sensors 10 at fixed intervals and is received by the collection device 30 is shown. For the conventional technology, the result of ETA is shown. That is, the result of ETA is shown when no correction is applied. As shown in FIG. 7, in the conventional technology, the error distribution extends to 2 μs or the like in addition to a large error of about 10 μs. This is considered to be caused by a clock error, a communication delay, a reception processing delay, and the like.

On the other hand, when the correction based on the estimation of the event detection time as in the present embodiment has been applied, the data is collected around an error of 0 μs. In this manner, because the sensor 10 only needs to transmit the detection result, the circuit configuration can be simplified, the costs can be reduced, and the power consumption can be reduced. Also, even when the sensor 10 retransmits the detection result, the relationship is obtained according to the present process, so that the influence of the clock error is reduced.

Next, an example of data transmission in the transmission terminal 20 will be described with reference to FIGS. 8 to 11.

Figure 8:
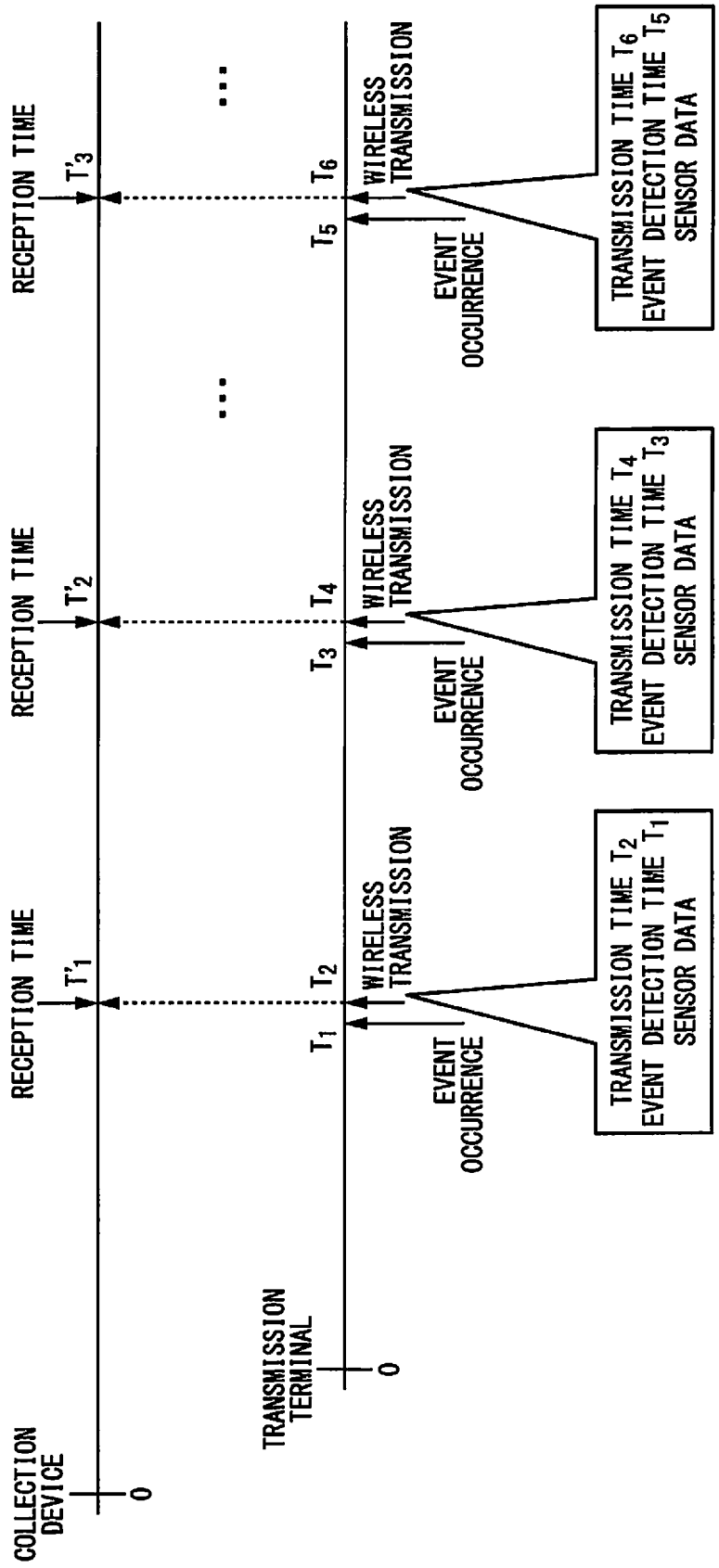
FIG. 8 is a diagram showing a specific example of a first transmission method performed by a transmission terminal according to the first embodiment.

FIG. 8 is a diagram showing a specific example of the first transmission method performed by the transmission terminal 20 according to the first embodiment. The first transmission method is a method in which the transmission terminal 20 transmits an event detection time, a transmission time, and sensor data to the collection device 30 in a single transmission process at a timing when a random period of time has elapsed after the occurrence of the event. More specifically, the transmission terminal 20 determines the transmission time of the event detection time after the occurrence of the event and transmits transmission data including the event detection time, the sensor data, and the transmission time to the collection device 30 at the determined time. The collection device 30 generates a reception time when the transmission data transmitted from the transmission terminal 20 has been received.

The first transmission method shown in FIG. 8 will be described as an example when the transmission terminal 20 determines an event detection time as a time $T_1$ and transmits information of the event detection time $T_1$ at the timing of a time $T_2$. In this case, the transmission terminal 20 generates transmission data including the "event detection time $T_1$", a "transmission time $T_2$", and "sensor data" and transmits the generated transmission data to the collection device 30. The collection device 30 generates the reception time $T'_1$ when the transmission data transmitted from the transmission terminal 20 has been received. In this manner, in the first transmission method, the transmission terminal 20 determines the event detection time after the occurrence of the event and transmits transmission data in which other necessary sensor data and the transmission time are combined to the collection device 30. However, there may be a case in which a microprocessor cannot include its own exact transmission time in transmission data at the time of transmission or the like.

Figure 9:
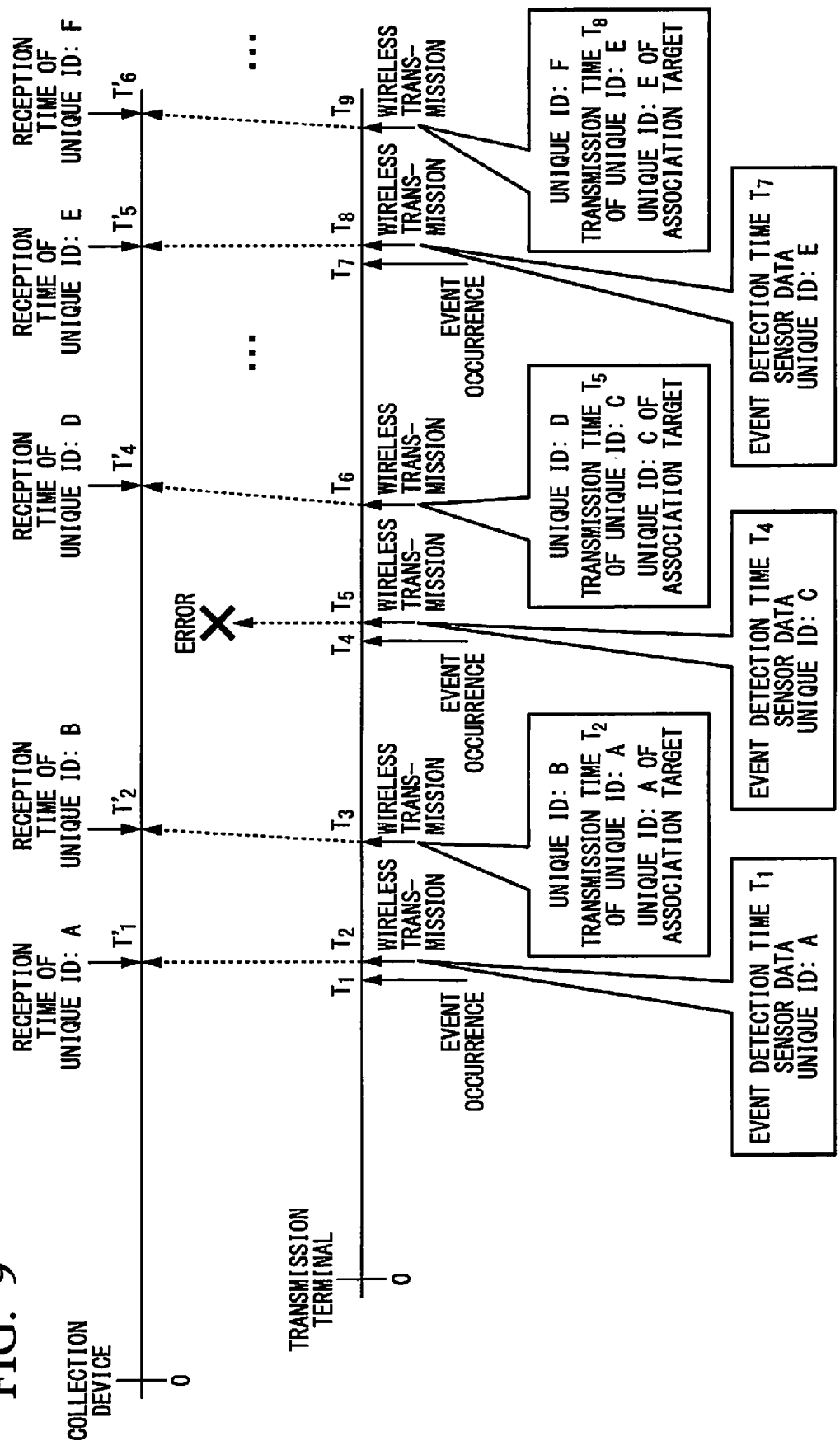
FIG. 9 is a diagram showing a specific example of a second transmission method performed by the transmission terminal according to the first embodiment.

FIG. 9 is a diagram showing a specific example of the second transmission method. The second transmission method is a method in which the transmission terminal 20 separately transmits an event detection time and a transmission time to the collection device 30 at a timing when a random period of time has elapsed after the occurrence of an event. More specifically, the transmission terminal 20 first transmits transmission data including an event detection time, sensor data, and a unique ID for identifying transmission data to the collection device 30 after the occurrence of the event. The collection device 30 generates a reception time when the transmission data transmitted from the transmission terminal 20 has been received. Next, the transmission terminal 20 determines a transmission time at the time of transmission of transmission data or after transmission thereof. Then, at the next transmission timing, the transmission terminal 20 transmits transmission data including the determined transmission time, a unique ID for identifying transmission data to be associated, and a unique ID for identifying transmission data to be currently transmitted to the collection device 30.

The next transmission timing is a timing at which a predetermined period of time has elapsed from the transmission of transmission data including information of an event detection time. For example, the next transmission timing may be after the transmission time is determined by the communication time determiner 273 and may be any timing if the next transmission timing is a random timing at which transmission is possible. The unique ID for identifying the transmission data to be associated is identification information for associating a reception time of the transmission data with a transmission time of the transmission data.

The second transmission method shown in FIG. 9 will be described as an example when the transmission terminal 20 determines an event detection time as a time $T_1$ and transmits information of the event detection time $T_1$ at the timing of a time $T_2$. In this case, the transmission terminal 20 generates transmission data including the "event detection time $T_1$", "sensor data", and a "unique ID: A" for identifying the transmission data and transmits the generated transmission data to the collection device 30. When the transmission data transmitted from the transmission terminal 20 has been received, the collection device 30 generates a "reception time $T'_1$" that is a reception time of the transmission data including the unique ID: A. Next, the transmission terminal 20 determines a transmission time at the time of transmission of transmission data or after transmission thereof. This transmission time is assumed to be $T_2$. Then, at the next transmission timing, the transmission terminal 20 generates transmission data including a "transmission time $T_2$" of the unique ID: A, the "unique ID: A" for identifying transmission data to be associated, and a "unique ID: B" for identifying transmission data to be currently transmitted and transmits the generated transmission data to the collection device 30. Thereby, the collection device 30 can associate a transmission time "transmission time $T_2$" of the transmission data including the "event detection time $T_1$" with a previously received "reception time $T'_1$" on the basis of the "unique ID: A" included in the received transmission data. In this manner, the second transmission method is used when the transmission time of the information of the "event detection time" is not determined at the time of transmission.

Figure 10:
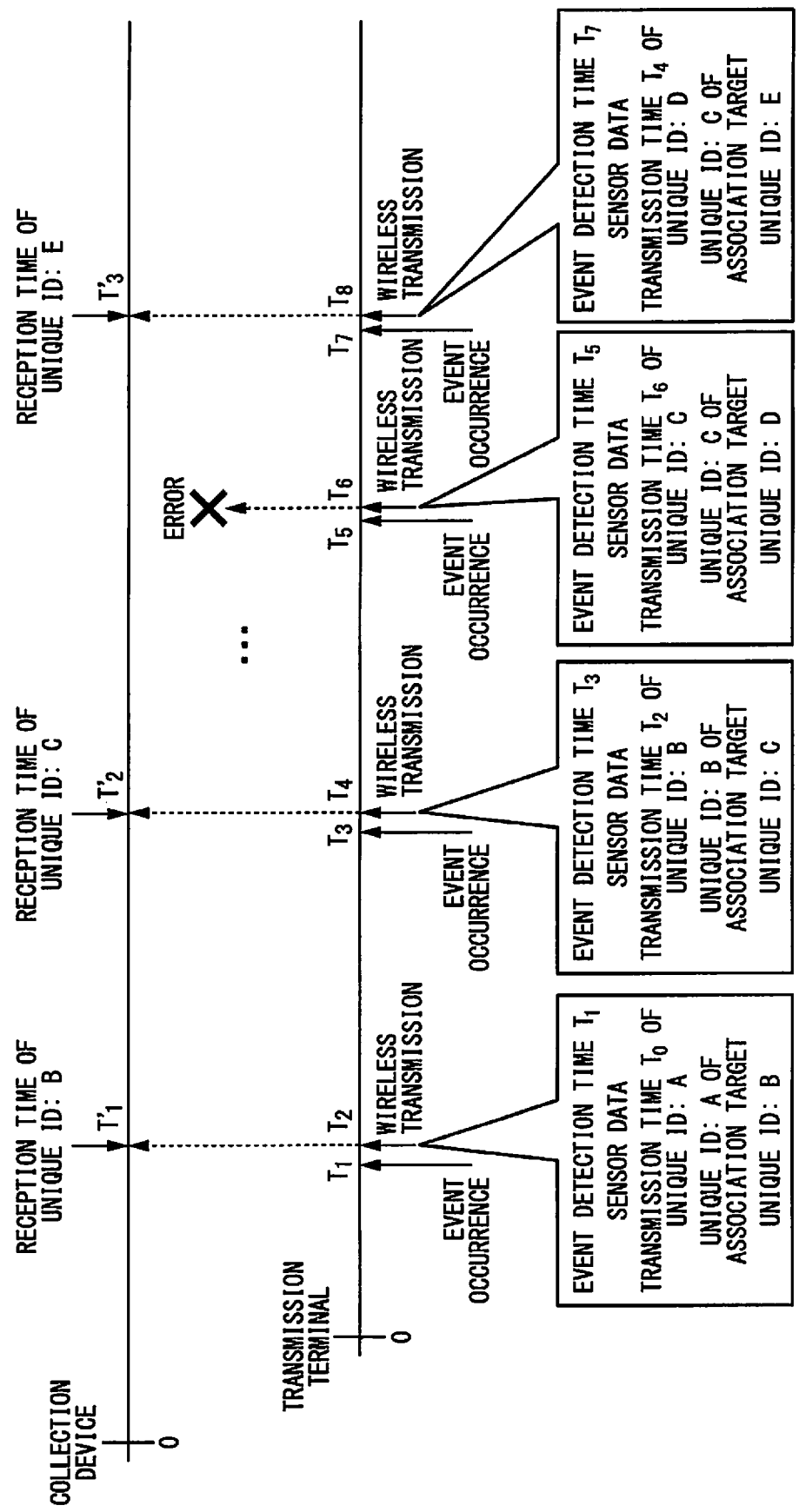
FIG. 10 is a diagram showing a specific example of a third transmission method performed by the transmission terminal according to the first embodiment.

FIG. 10 is a diagram showing a specific example of a third transmission method. The third transmission method is a method in which the transmission terminal 20 transmits a transmission time of a previous event detection time, a current event detection time, and sensor data to the collection device 30 at a timing when a random period of time has elapsed after the occurrence of an event. More specifically, the transmission terminal 20 first transmits transmission data including the current event detection time, the sensor data, a unique ID for identifying transmission data, a transmission time of information of the previous event detection time, and a unique ID for identifying transmission data to be associated to the collection device 30 after the occurrence of the event. The collection device 30 generates a reception time when the transmission data transmitted from the transmission terminal 20 has been received. Next, the transmission terminal 20 determines a transmission time at the time of transmission of transmission data or after transmission thereof. Then, after the next event occurs, the transmission terminal 20 transmits transmission data including a transmission time of a previous event detection time, sensor data, a current event detection time, a unique ID for identifying transmission data to be currently transmitted, and a unique ID for identifying transmission data to be associated to the collection device 30.

The third transmission method shown in FIG. 10 will be described as an example when the transmission terminal 20 determines an event detection time as a time $T_1$ and transmits information of the event detection time $T_1$ at a timing of a time $T_2$. In this case, the transmission terminal 20 generates transmission data including the "event detection time $T_1$", "sensor data", a "transmission time $T_0$" of the transmission data with the unique ID of "A", a "unique ID: A" for identifying transmission data to be associated, and a "unique ID: B" for identifying transmission data and transmits the generated transmission data to the collection device 30. When the transmission data including "unique ID: B" transmitted from the transmission terminal 20 has been received, the collection device 30 generates a "reception time $T'$ i" of the unique ID: B. Next, the transmission terminal 20 determines a transmission time at the time of transmission of transmission data or after transmission thereof. This transmission time is assumed to be $T_2$. Then, after the next event occurs, the transmission terminal 20 generates transmission data including a "transmission time $T_3$" of an event detection time, sensor data, a "transmission time $T_2$" of transmission data with a unique ID of "B", a "unique ID: B" for identifying transmission data to be associated, and a "unique ID: C" for identifying transmission data to be currently transmitted and transmits the generated transmission data to the collection device 30.

Thereby, the collection device 30 can associate the "transmission time $T_2$" which is the transmission time of transmission data including an "event detection time $T_1$" with a "reception time $T'_1$" that has been transmitted at the "transmission time $T_2$" and received on the basis of the "unique ID: B" included in the received transmission data. In this manner, the third transmission method is used when the transmission time of the information of the "event detection time" is not determined at the time of transmission, as in the second transmission method. The third transmission method is different from the second transmission method in that the information of a transmission time associated with the information of an event detection time that has already been transmitted is included in transmission data of a subsequent event.

In both the transmission methods shown in FIGS. 9 and 10, the associated event detection time and transmission time are not included in the same packet. Thus, a transmission processing error, packet loss, and order are assumed to be changed according to transmission. Therefore, in the second transmission method and the third transmission method described above, it is possible to easily perform the association by adding a unique ID, a counter value of the number of transmissions, and the like in order to associate the transmission packet with the transmission time. Accordingly, even when the transmission order of the packet corresponding to the event is changed, the association is possible. However, the unique ID is not essential when the correspondence can be understood without the unique ID.

Figure 11:
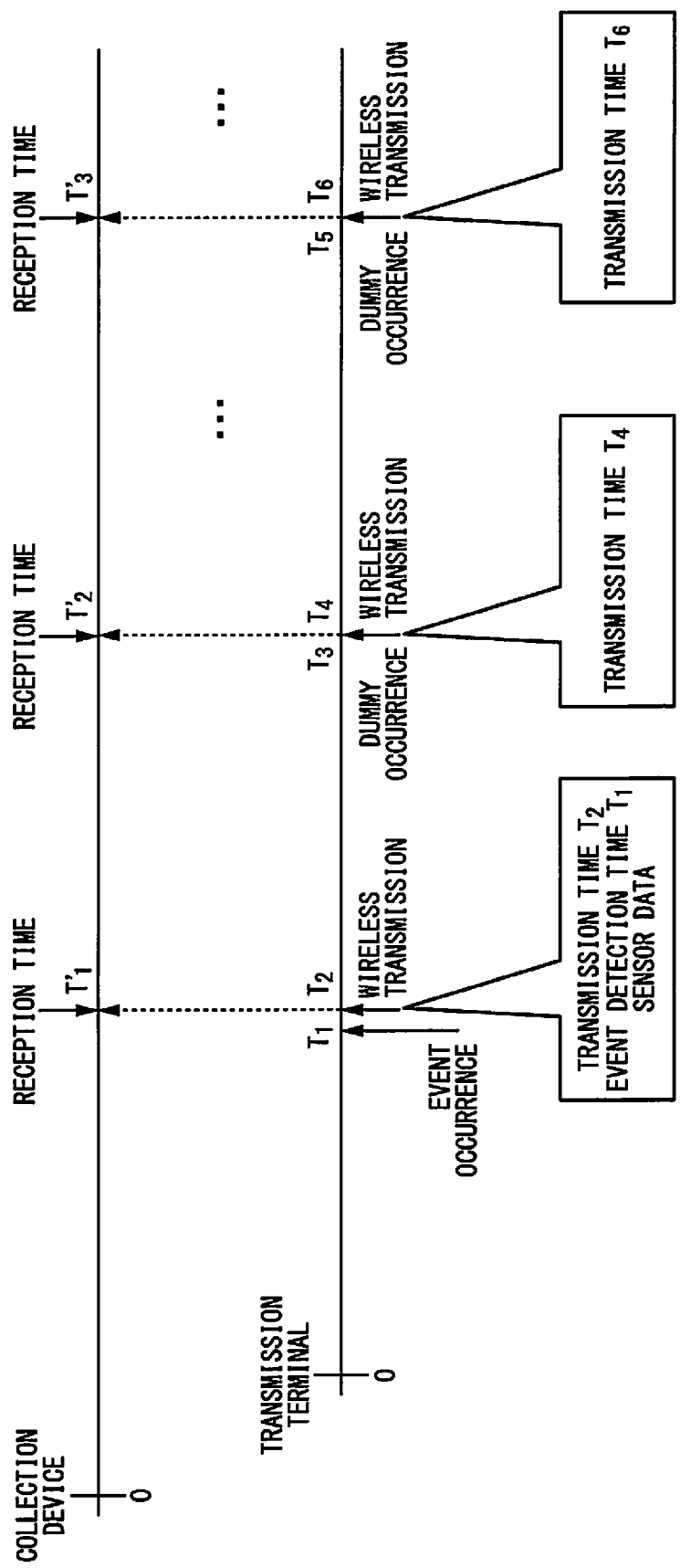
FIG. 11 is a diagram showing a specific example of a fourth transmission method performed by the transmission terminal according to the first embodiment.

FIG. 11 is a diagram showing a specific example of a fourth transmission method. The fourth transmission method is a method in which the transmission terminal 20 transmits a transmission time to the collection device 30 by causing a dummy event to occur before and after the occurrence of an event. The dummy event is an event whose occurrence has not been detected by the event signal generator 271 and which has not actually occurred. That is, the dummy event is a virtual event. More specifically, the transmission terminal 20 first transmits transmission data including an event detection time, a transmission time, and sensor data to the collection device 30 before and after the occurrence of the event. Next, the transmission terminal 20 transmits transmission data including the transmission time to the collection device 30 after the occurrence of the dummy event. The communication time determiner 273 may cause the dummy event to occur, the communicator 274 may cause the dummy event to occur, or the transmission terminal 20 may cause the dummy event to occur by newly providing a dummy event generator.

The fourth transmission method shown in FIG. 11 will be described as an example when the transmission terminal 20 determines an event detection time as a time $T_1$ and transmits information of the event detection time $T_1$ at a timing of a time $T_2$. In this case, the transmission terminal 20 generates transmission data including an "event detection time $T_1$", a "transmission time $T_2$", and "sensor data" and transmits the generated transmission data to the collection device 30. The collection device 30 generates a "reception time $T'_1$". Subsequently, when no event is detected at a timing when a predetermined period of time has elapsed, the transmission terminal 20 causes a dummy event to occur, generates transmission data including a transmission time "transmission time $T_4$" at the next transmission timing, and transmits the generated transmission data to the collection device 30. Thus, the fourth transmission method is used when an event occurs only once within a certain period.

Also, although a configuration in which the transmission terminal 20 transmits the event detection time, the transmission time, and the sensor data to the collection device 30 in a single transmission process as in the first transmission method in the fourth transmission method shown in FIG. 11 is shown, the event detection time and the transmission time may be transmitted at different timings.

Although an event occurs a plurality of times and correction can be performed from the relationship between a plurality of time stamps (a transmission time and a reception time) in the example shown in FIGS. 8 to 10, a relationship is not obtained if the event occurs once. Also, when an event occurrence interval is long, there is uncertainty in the relationship. Therefore, in the fourth transmission method, transmission data is transmitted after the occurrence of an event as shown in FIG. 11 and the transmission terminal 20 generates a dummy event, transmits transmission data, and increases the transmission time and the reception time to enhance an estimation system. It is only necessary to include at least the transmission time in the transmission data transmitted by the transmission terminal 20 in the dummy event.

In the case of FIG. 9 or 10, it is also possible to add a unique ID to the transmission data to be transmitted in the dummy event and associate them. A dummy operation can be performed according to the density of event detection or can be performed at a predetermined timing. The transmission terminal 20 may use a combination of the first to fourth transmission methods shown in FIGS. 8 to 11. For example, the transmission terminal 20 may perform transmission in the first transmission method at the time of first transmission and perform transmission in the second transmission method at the time of second transmission.

Figure 12:
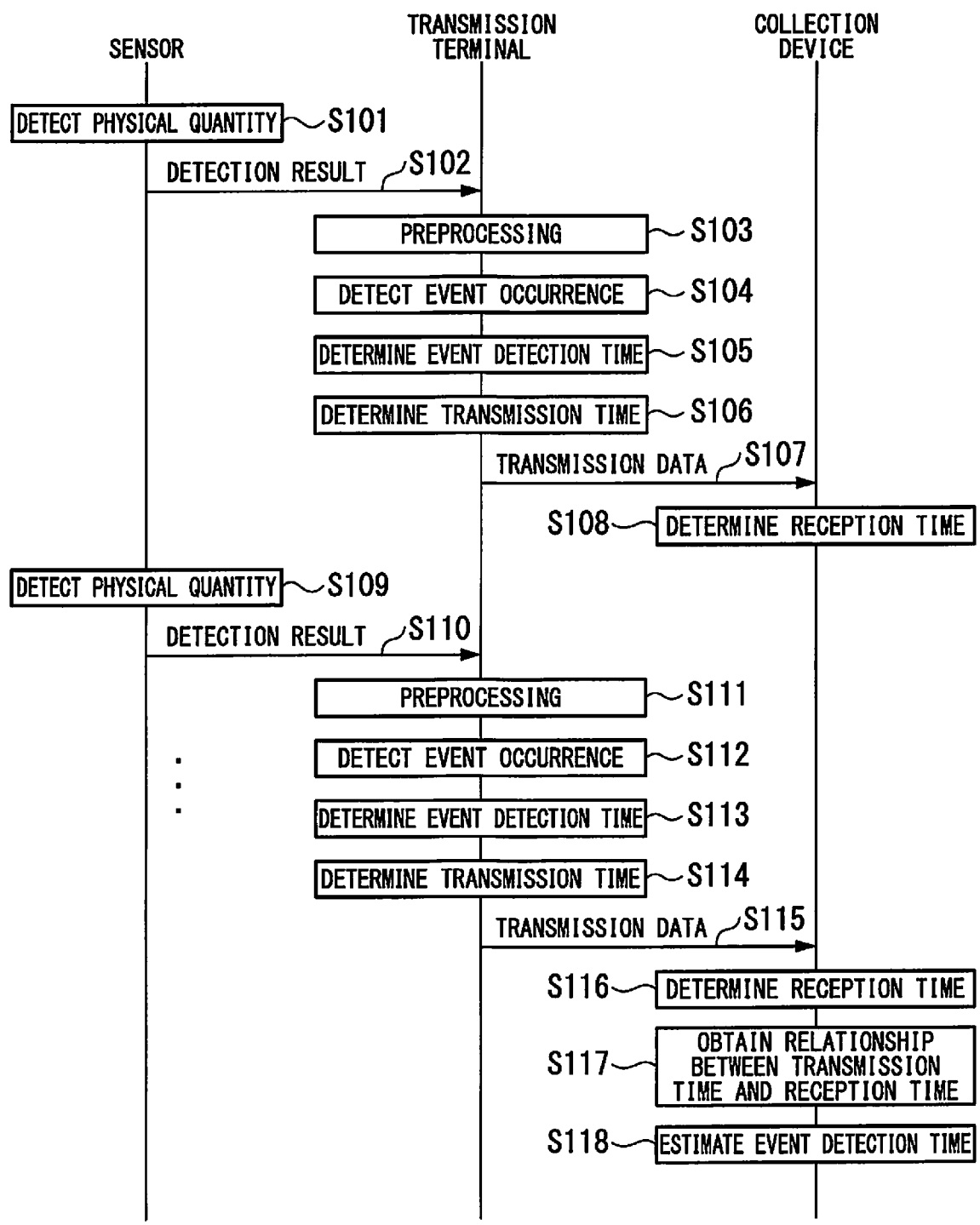
FIG. 12 is a sequence diagram showing a flow of a process performed by the sensor system according to the first embodiment.

FIG. 12 is a sequence diagram showing a flow of a process performed by the sensor system 100 according to the first embodiment. An example in which the transmission terminal 20 transmits transmission data in the first transmission method will be described with reference to FIG. 12.

The sensor 10 detects a physical quantity (step S101). The sensor 10 converts the detected physical quantity into an electrical signal. The sensor 10 transmits the electrical signal indicating a detection result to the transmission terminal 20 (step S102). The receiver 21 of the transmission terminal 20 receives the electrical signal transmitted from the sensor 10. The transmission terminal 20 performs preprocessing on the received electrical signal (step S103). The event signal generator 271 detects the occurrence of an event on the basis of a preprocessed signal (step S104). The event signal generator 271 outputs a first gate signal to the event time determiner 272. The event time determiner 272 determines a time when the first gate signal has been input as an event detection time (step S105). The event time determiner 272 outputs information of the determined event detection time to the communicator 274. Also, the event time determiner 272 also outputs the sensor data obtained from the sensor 10 to the communicator 274.

The communication time determiner 273 inputs the time information generated by the time information generator 26. The communication time determiner 273 determines the transmission time on the basis of the input time information (step S106). The communication time determiner 273 outputs information of the determined transmission time to the communicator 274. The communicator 274 generates transmission data including an event detection time and sensor data output from the event time determiner 272 and the transmission time output from the communication time determiner 273.

The communicator 274 transmits the generated transmission data to the collection device 30 (step S107).

The communicator 33 of the collection device 30 receives the transmission data transmitted from the transmission terminal 20. The communicator 33 outputs the received transmission data to the reception time determiner 34 and the time information processor 35. The reception time determiner 34 determines the reception time on the basis of the time information generated by the time information generator 32 and the transmission data output from the communicator 33 (step S108).

Specifically, the reception time determiner 34 determines a time indicated by the time information of a point in time at which the transmission data has been obtained as a reception time. The reception time determiner 34 outputs information of the determined reception time to the time information processor 35. The time information processor 35 saves the transmission data output from the communicator 33 and the information of the reception time output from the reception time determiner 34 in association in the storage unit.

When a fixed period of time has elapsed, the sensor 10 detects a physical quantity (step S109). The sensor 10 converts the detected physical quantity into an electrical signal. The sensor 10 transmits an electrical signal indicating a detection result to the transmission terminal 20 (step S110). The receiver 21 of the transmission terminal 20 receives the electrical signal transmitted from the sensor 10. The transmission terminal 20 performs preprocessing on the received electrical signal (step S111). The event signal generator 271 detects the occurrence of an event on the basis of the preprocessed signal (step S112). The event signal generator 271 outputs a first gate signal to the event time determiner 272. The event time determiner 272 determines a time when the first gate signal has been input as an event detection time (step S113).

The communication time determiner 273 inputs the time information generated by the time information generator 26. The communication time determiner 273 determines a transmission time on the basis of the input time information (step S114).

The communication time determiner 273 outputs information of the determined transmission time to the communicator 274. The communicator 274 generates transmission data including an event detection time and sensor data output from the event time determiner 272 and the transmission time output from the communication time determiner 273.

The communicator 274 transmits the generated transmission data to the collection device 30 (step S115).

The communicator 33 of the collection device 30 receives the transmission data transmitted from the transmission terminal 20. The communicator 33 outputs the received transmission data to the reception time determiner 34 and the time information processor 35. The reception time determiner 34 determines a reception time on the basis of the time information generated by the time information generator 32 and the transmission data output from the communicator 33 (step S116).

The reception time determiner 34 outputs information of the determined reception time to the time information processor 35. The time information processor 35 saves the transmission data output from the communicator 33 and the information of the reception time output from the reception time determiner 34 in association in the storage unit.

The time information processor 35 obtains a relationship between the transmission time and the reception time on the basis of information of a plurality of transmission times and information of a plurality of reception times saved in the storage unit (step S117).

Specifically, the time information processor 35 obtains the graph shown in FIG. 6 using the information of the plurality of transmission times and the information of the plurality of reception times. Subsequently, the time information processor 35 estimates the event detection time in the collection device 30 using the relationship between the transmission time and the reception time obtained from the obtained graph and the event detection time (step S118).

Figure 13:
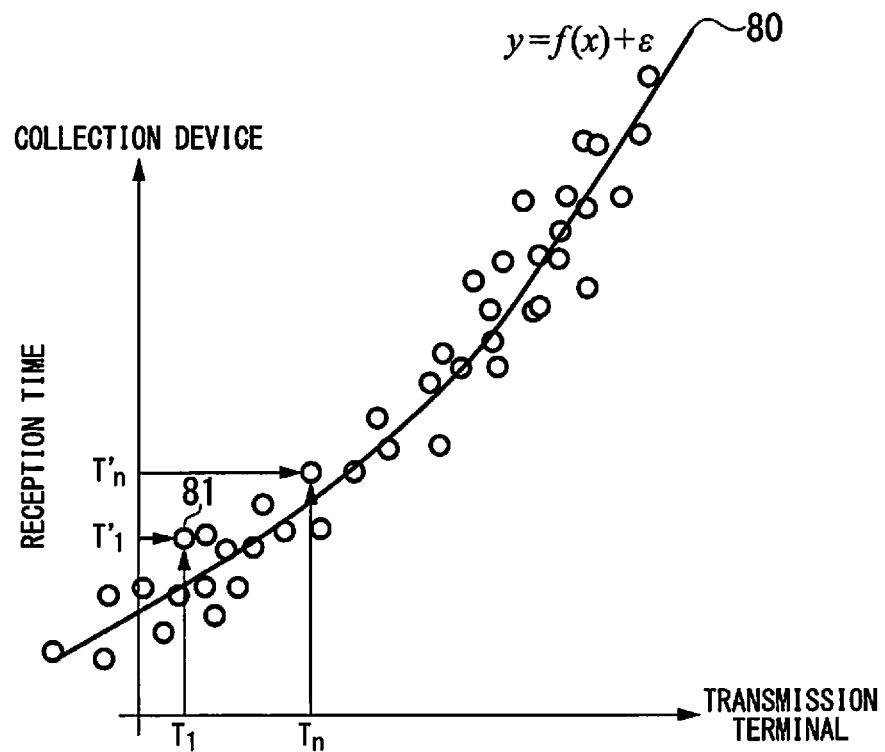
FIG. 13 is an explanatory diagram showing a specific process of the time information processor according to the first embodiment.
Figure 14:
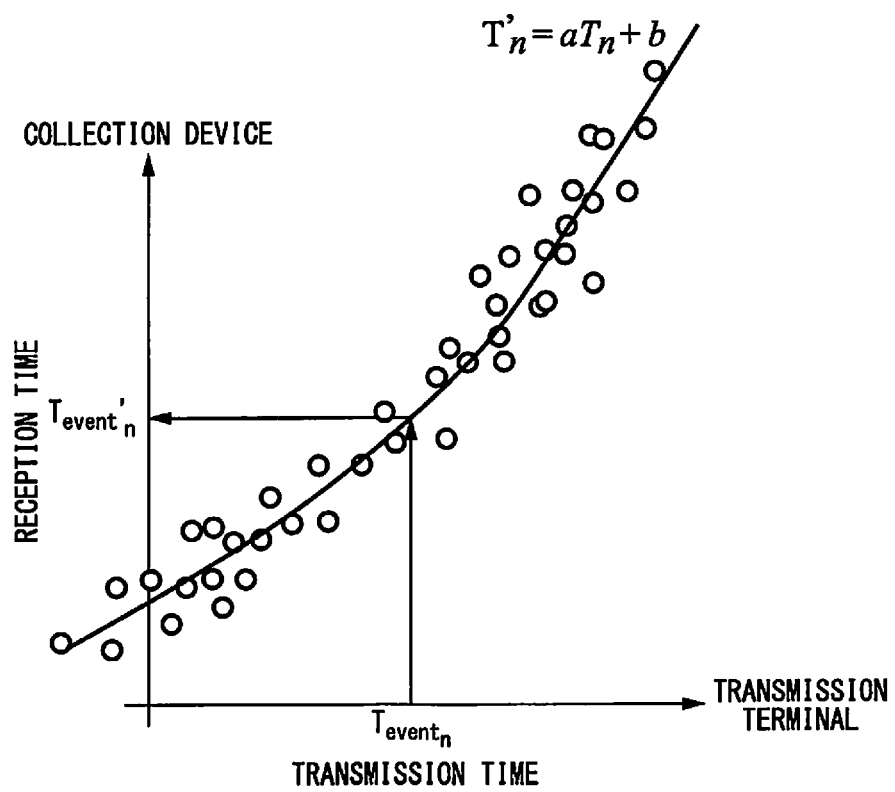
FIG. 14 is an explanatory diagram showing a specific process of the time information processor according to the first embodiment.
Figure 15:
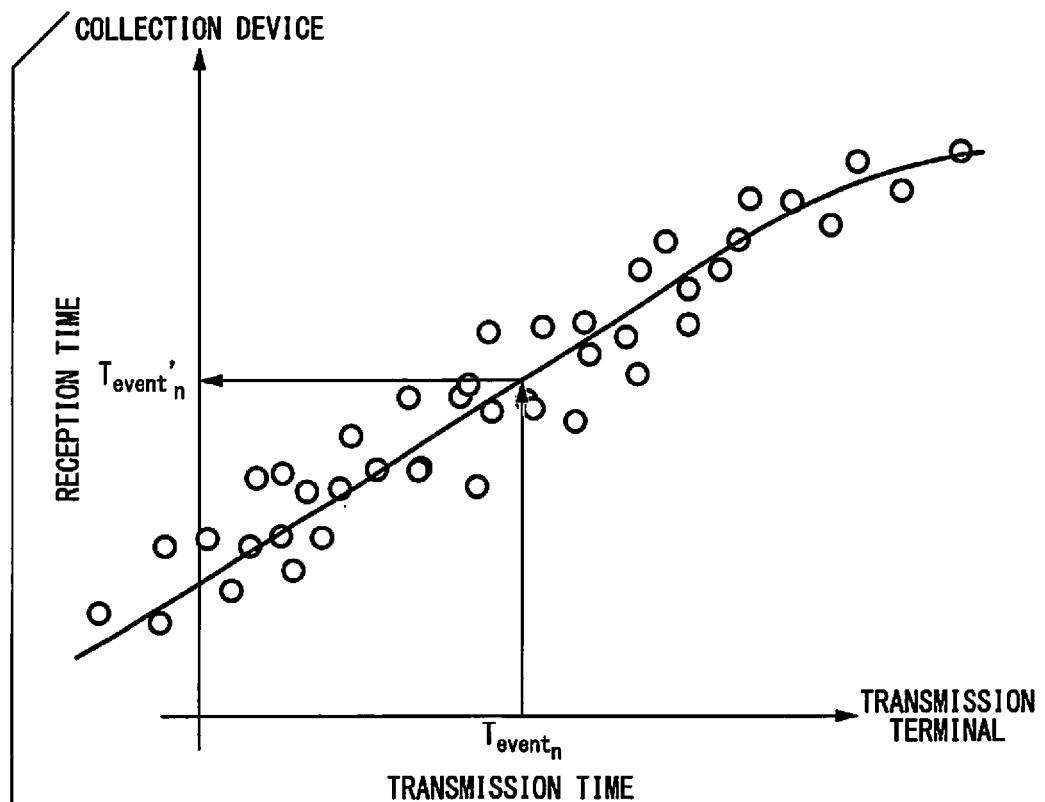
FIG. 15 is an explanatory diagram showing a specific process of the time information processor according to the first embodiment.
Figure 15:
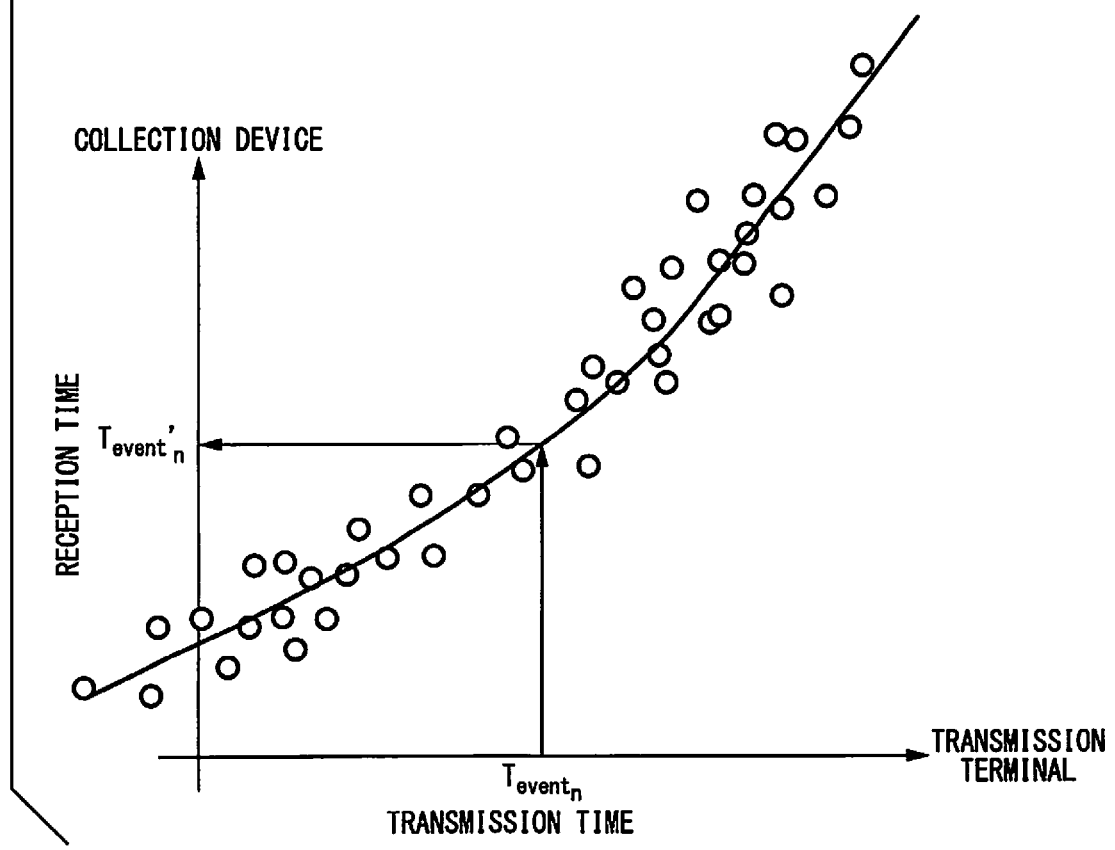

Hereinafter, a specific process of the time information processor 35 will be described with reference to FIGS. 13 to 15. FIGS. 13 to 15 are explanatory diagrams showing a specific process of the time information processor 35 according to the first embodiment. Also, in FIGS. 13 to 15, a propagation period of time between the transmission terminal 20 and the collection device 30 is assumed to be known or negligibly small.

The graph shown in FIG. 13 is assumed to be obtained on the basis of a transmission time of the transmission terminal 20 and a reception time of the collection device 30 obtained when time processing as shown in FIG. 5 has been performed. In FIG. 13, y represents a reception time (T'), f(x) represents a model function, x represents a transmission time (T), and ε represents an error. A line 80 is a line representing the relationship between the transmission time of the transmission terminal 20 and the reception time of the collection device 30. This line 80 can be obtained by the regression analysis as described above. As shown in FIG. 13, a position of the point 81 obtained by a corresponding relationship between the transmission time and the reception time is slightly deviated from the line 80. This deviation is an error. A unique clock is embedded in each of the transmission terminal 20 and the collection device 30. Thus, the time of the clock is deviated if power-on timings are different and the time of the clock is deviated if the speeds of clocks are not exactly identical. Also, because the accuracy of the transmission time and the accuracy of the reception time also have an influence, there are not a few errors as shown in FIG. 13.

The relationship between the clock of the transmission terminal 20 and the clock of the collection device 30 can be represented by y=f(x)+ε. In this case, when data such as $(T_1, T'_1), \ldots, (T_n, T'_n)$ is obtained, theoretical values become $(T_1, f(T'_1)), \ldots, (T_n, f(T'_n))$. At this time, the error is $|T'_i - f(T_i)|$. i is an integer of 1 or more. Then, the time information processor 35 estimates the event detection time by finding f for minimizing J in the following Eq. (1). When a propagation time is known, the time information processor 35 corrects a result to perform estimation.

[Math. 1]

$$J = \sum_{i=1}^{n} (T'_i - f(T_i)) \qquad \text{Eq. (1)}$$

This will be described in more detail with reference to FIG. 14.

When $f(T_n) = aT_n + b$, the time information processor 35 calculates a and b for minimizing J in the above Eq. (1) on the basis of the following Eqs. (2).

[Math. 2]

$$a = \frac{n\sum_{i=1}^{n} T_i T'_i - \sum_{i=1}^{n} T_i \sum_{i=1}^{n} T'_i}{n\sum_{i=1}^{n} T_i^2 - (\sum_{i=1}^{n} T_i)^2} \qquad \text{Eqs. (2)}$$

$$b = \frac{\sum_{i=1}^{n} T_i^2 \sum_{i=1}^{n} T'_i - \sum_{i=1}^{n} T_i T'_i \sum_{i=1}^{n} T_i}{n\sum_{i=1}^{n} T'^2_i - (\sum_{i=1}^{n} T_i)^2}$$

If $T'_n = aT_n + b$ is known, the time of the clock of the collection device 30 becomes $T_{event'_n} a T event_n + b$ as shown in FIG. 14.

Although a case in which there is a single transmission terminal 20 has been described as an example in FIGS. 13 and 14, the time information processor 35 obtains a time relationship between each transmission terminal 20 and the collection device 30 as shown in FIG. 15 when there are a plurality of transmission terminals 20 as in a case in which the number of transmission terminals 20 is one. Also, when the propagation time has been estimated or measured in advance or when there is a known fixed error, correction can be made with $T'_n = aT_n + b + c$ and known c.

According to the sensor system 100 configured as described above, a plurality of transmission times and a plurality of reception times are input and a relationship between the transmission time and the reception time is obtained. The transmission time is based on the time in the transmission terminal 20. The reception time is based on the time in the collection device 30. Therefore, the collection device 30 can acquire information for estimating (correcting) the event detection time by obtaining the relationship between the transmission time and the reception time. The collection device 30 estimates an event detection time using the acquired information. Thereby, errors related to a clock or errors due to priority processing in a microprocessor are averaged as compared with the case in which only the reception time stamp (reception time) is used or the estimation method such as ETA is used. Thus, the error in the event detection time can be reduced. As a result, the synchronization accuracy can be improved.

Hereinafter, modified examples of the sensor system 100 according to the first embodiment will be described.

The event signal generator 271 may be configured to detect an event on the basis of information inside the transmission terminal 20. The information inside the transmission terminal 20 includes time information, errors, and the like. Thus, when the transmission terminal 20 detects an event on the basis of the information inside the transmission terminal 20, the sensor system 100 may not include the sensor 10. When the sensor system 100 does not include the sensor 10, the transmission terminal 20 may be configured to include a clock oscillator 25, a time information generator 26, and a signal processor 27.

Some functions of the collection device 30 may be implemented in another device (for example, a server located in a network higher than the collection device 30). For example, the time information processor 35 provided in the collection device 30 may be mounted on another device. In this case, the collection device 30 determines data collection and reception times. In other devices, the time information processor 35 estimates the event detection time. The collection device 30 is an aspect of the time information processing device.

Although a configuration in which the collection device 30 obtains a graph indicating the relationship between the transmission time and the reception time corresponding to the transmission time is shown in the present embodiment, the collection device 30 may be configured to calculate a time difference between transmission times and a time difference between reception times corresponding to the transmission times and obtain a graph showing a relationship between the calculated time difference between the transmission times and the calculated time difference between the reception times corresponding to the transmission times. The time difference between the transmission times is, for example, a time difference between transmission times that are adjacent to each other in a plurality of transmission times.

As an example, when the transmission times are $T_1$, $T_2$, $T_3$, $T_4$, and the like, a time difference between $T_1$ and $T_2$, a time difference between $T_2$ and $T_3$, and a time difference between $T_3$ and $T_4$ are time differences between transmission times adjacent to each other. The same applies to time differences between reception times.

Second Embodiment

In the second embodiment, a configuration in which the sensor system 100 shown in the first embodiment is applied to position location of an elastic wave generation source will be described. That is, the occurrence of an event is detection of elastic waves in the second embodiment.

Figure 16:
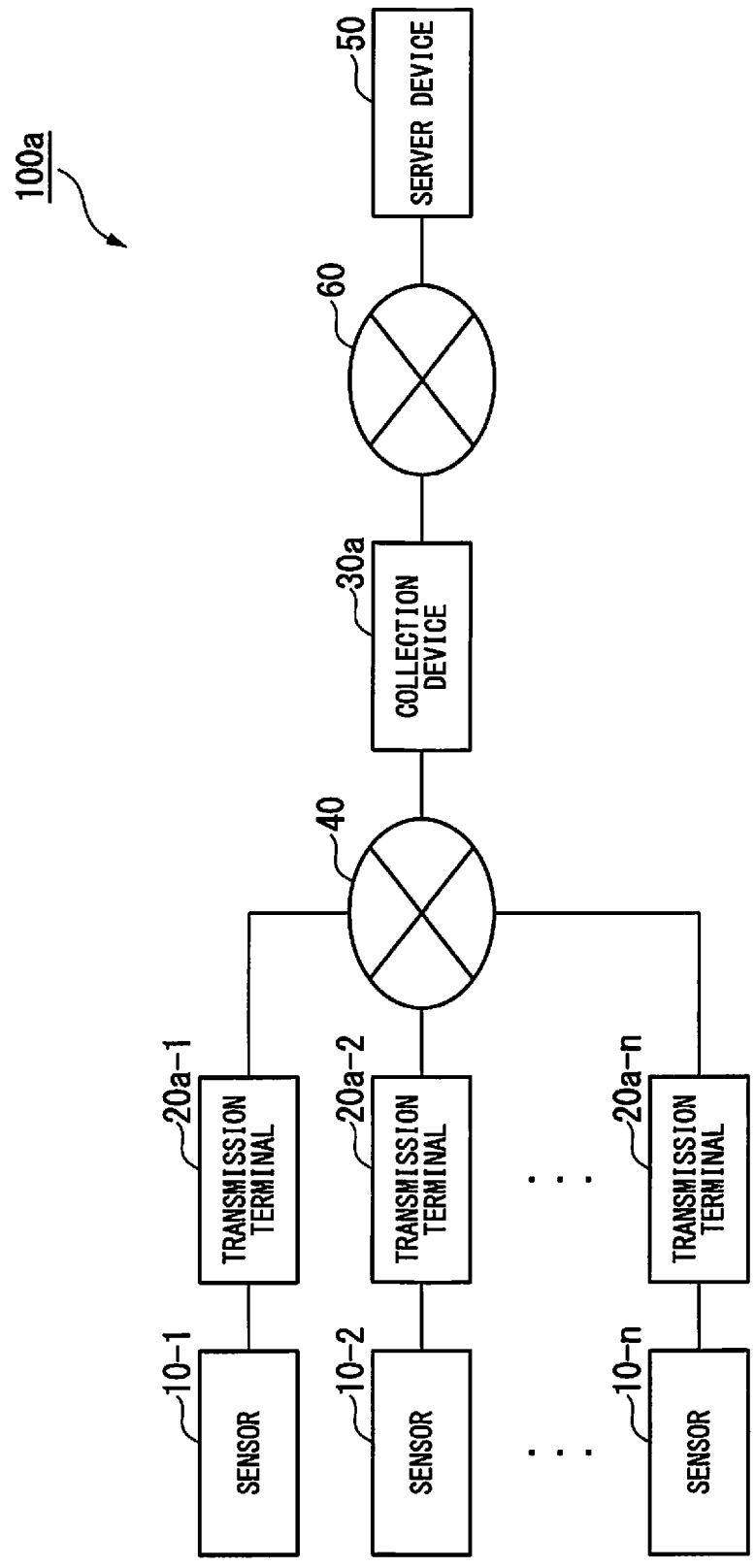
FIG. 16 is a diagram showing a system configuration of a sensor system according to a second embodiment.

FIG. 16 is a diagram showing a system configuration of a sensor system 100a according to the second embodiment. The sensor system 100a includes a plurality of sensors 10-1 to 10-n (n is an integer of 3 or more), a plurality of transmission terminals 20a-1 to 20a-n, a plurality of collection devices 30a-1 to 30a-n, and a server device 50. The sensor 10-1 and the transmission terminal 20a-1, the sensor 10-2 and the transmission terminal 20a-2, and the sensor 10-n and the transmission terminal 20a-n are connected by wire.

Each of the plurality of transmission terminals 20a-1 to 20a-n and the collection device 30a are wirelessly connected via the network 40. The collection device 30a and the server device 50 are connected with priority or wirelessly via the network 60. For example, the network 60 may be a LAN or the Internet.

In the following description, the sensors 10-1 to 10-n will be described as sensors 10 when they are not distinguished. In the following description, the transmission terminals 20a-1 to 20a-n will be described as transmission terminals 20a when they are not distinguished. In the following description, the collection devices 30a-1 to 30a-n will be described as collection devices 30a when they are not distinguished. Although a case in which one sensor 10 is connected to one transmission terminal 20a is shown in FIG. 16, a plurality of sensors 10 may be connected to one transmission terminal 20a. Also, when the functional units in the device are described separately, the functional units are distinguished by adding branch numbers thereto. For example, when functional units included in the transmission terminal 20a-1 are described, a branch number of −1 is attached to distinguish the functional units from those of other devices.

The sensor 10 is installed in a structure. For example, the sensor 10 is installed on a concrete floor slab of a bridge. The sensor 10 has a piezoelectric element and detects elastic waves generated from the inside of the structure. The sensor 10 is installed at a position where elastic waves can be detected. For example, the sensor 10 is installed on any one of a front surface, a side surface, and a bottom surface of a structure. The sensor 10 converts the detected elastic waves into an electric signal that is a voltage signal. The sensor 10 outputs the electrical signal to the transmission terminal 20a. In the second embodiment, the sensor 10 will be described as an example of an AE sensor or an acceleration sensor.

Although a bridge made of concrete will be described as an example of a structure in the following description, the structure need not be limited to a bridge. The structure may be any structure as long as elastic waves are generated due to the occurrence or progress of a crack or an external impact (for example, rain, artificial rain, or the like). For example, the structure may be a rock. Bridges are not limited to structures laid on rivers, valleys, or the like, and also include various structures (for example, highway viaducts) provided above the ground and the like.

Next, the configuration of the transmission terminal 20*a* will be described. The transmission terminal 20*a* according to the second embodiment is similar to that according to the first embodiment except for the signal processor. Thus, only the signal processor 27*a* will be described.

Figure 17:
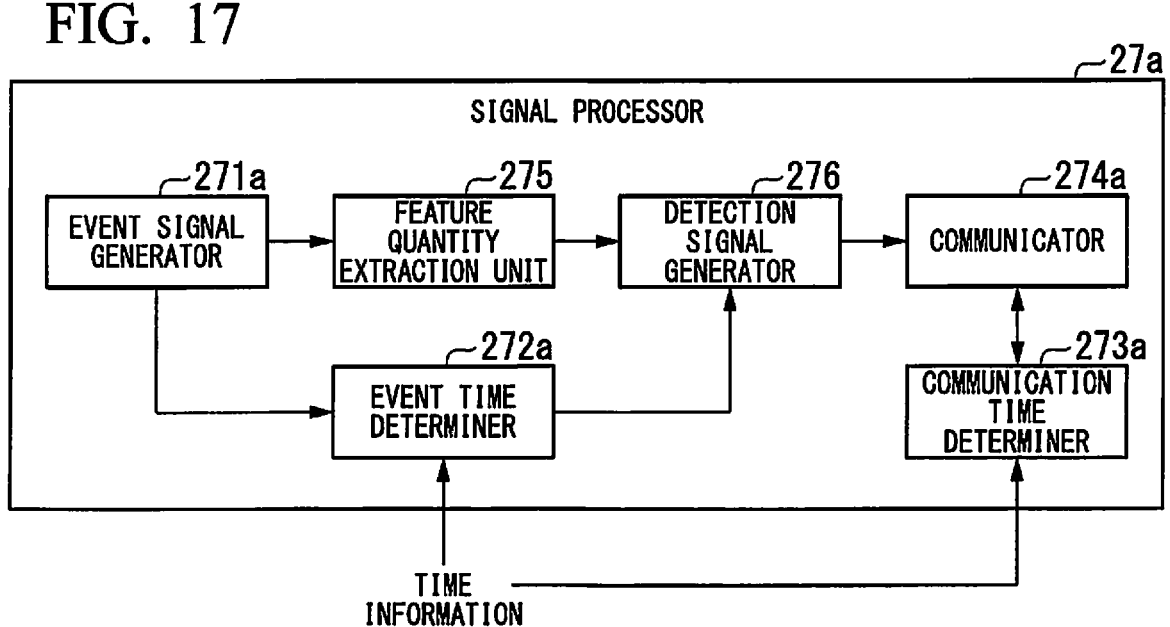
FIG. 17 is a schematic block diagram showing an internal configuration of a signal processor according to the second embodiment.

FIG. 17 is a schematic block diagram showing an internal configuration of the signal processor 27*a* according to the second embodiment.

The signal processor 27*a* includes an event signal generator 271*a*, an event time determiner 272*a*, a communication time determiner 273*a*, a communicator 274*a*, a feature quantity extraction unit 275, and a detection signal generator 276.

The event signal generator 271*a* performs a process similar to that of the event signal generator 271. The event signal generator 271*a* outputs a first gate signal or a second gate signal to the event time determiner 272*a* and the feature quantity extraction unit 275.

The event time determiner 272*a* performs a process similar to that of the event time determiner 272. The event time determiner 272*a* outputs information of an event detection time to the detection signal generator 276 so that a determined event detection time is associated with a feature quantity.

The communication time determiner 273*a* performs a process similar to that of the communication time determiner 273.

The communicator 274*a* is a communication interface that performs communication with the collection device 30*a* via the network 40. The communicator 274*a* inputs detection information output from the detection signal generator 276 and a transmission time output from the communication time determiner 273*a*. The communicator 274*a* may have a storage unit. The storage unit has, for example, a dual port RAM, and stores the detection information and the transmission time. The storage unit is not necessarily provided in the communicator 274*a* and may be provided in the transmission terminal 20*a*. The communicator 274*a* transmits the detection information and the transmission time to the collection device 30*a* at a predetermined timing according to wireless communication. A radio frequency band for use in communication of the communicator 274*a* is, for example, a band such as 2.4 GHz or 920 MHz. The communicator 274*a* can also transmit the detection information and the transmission time together or transmit the detection information and the transmission time separately at an appropriate timing.

The feature quantity extraction unit 275 extracts a feature quantity when the signal waveform continues on the basis of the gate signal output from the event signal generator 271*a*. The feature quantity is information indicating a feature of the signal. For example, the feature quantity includes an amplitude [mV] of the waveform of the signal, a rising time [μsec] of the gate signal, the duration [μsec] of the gate signal, a zero cross count number [times] of the duration waveform, signal energy [arb.], a frequency [Hz], and the like. The feature quantity extraction unit 275 inputs the feature quantity to the detection signal generator 276.

The detection signal generator 276 receives the feature quantity from the feature quantity extraction unit 275 and receives the event detection time from the event time determiner 272*a*. The detection signal generator 276 generates detection information in which the feature quantity is associated with the event detection time, and outputs the generated detection information to the communicator 274*a*.

Also, the detection signal generator 276 also outputs sensor data to the communicator 274*a* when the sensor data has been obtained from the event time determiner 272*a*.

Next, the hardware of the transmission terminal 20*a* will be described. The power of the transmission terminal 20*a* is supplied from an external power source, a primary battery, a secondary battery, a solar battery, an energy harvester, or the like. The transmission terminal 20*a* is implemented from an analog circuit and a digital circuit. The digital circuit is implemented by, for example, an FPGA or a microcomputer. The digital circuit may be implemented by a dedicated LSI. Also, the transmission terminal 20*a* may be equipped with a non-volatile memory such as a flash memory or a removable memory.

Figure 18:
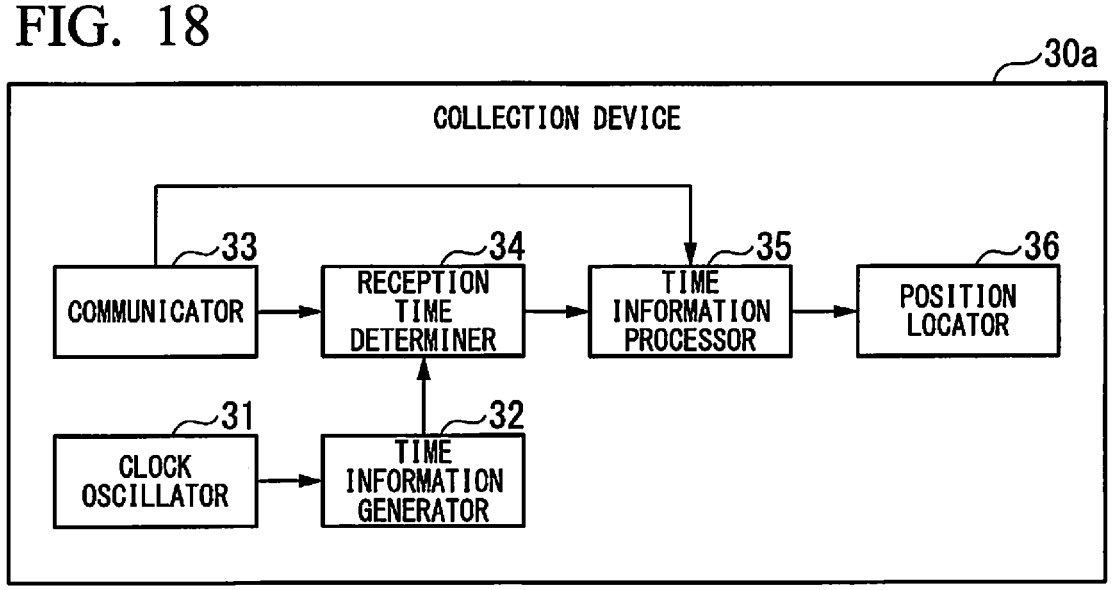
FIG. 18 is a schematic block diagram showing a function of a collection device according to the second embodiment.

FIG. 18 is a schematic block diagram showing a function of the collection device 30*a* according to the second embodiment.

The collection device 30*a* includes a CPU, a memory, an auxiliary storage device, and the like connected by a bus and executes a collection program. By executing the collection program, the collection device 30*a* functions as a device including a clock oscillator 31, a time information generator 32, a communicator 33, a reception time determiner 34, a time information processor 35, and a position locator 36. Also, all or some of the functions of the collection device 30*a* may be implemented using hardware such as an ASIC, a PLD, or an FPGA. Also, the collection program may be recorded on a computer-readable recording medium. The computer-readable recording medium is, for example, a flexible disk, a magneto-optical disk, a ROM, a portable medium such as a CD-ROM, or a storage device such as a hard disk built into a computer system. Also, the collection program may be transmitted and received via a telecommunication circuit.

A configuration of the collection device 30*a* is different from the configuration of the collection device 30 in that the position locator 36 is newly provided.

The collection device 30*a* is similar to the collection device 30 in terms of other configurations. Thus, the description of the whole of the collection device 30*a* will be omitted and the position locator 36 will be described.

The position locator 36 inputs a result of estimating an event detection time and detection information output from the time information processor 35. The position locator 36 locates a position of an elastic wave generation source on the basis of the result of estimating the event detection time and the detection information that have been input.

Figure 19:
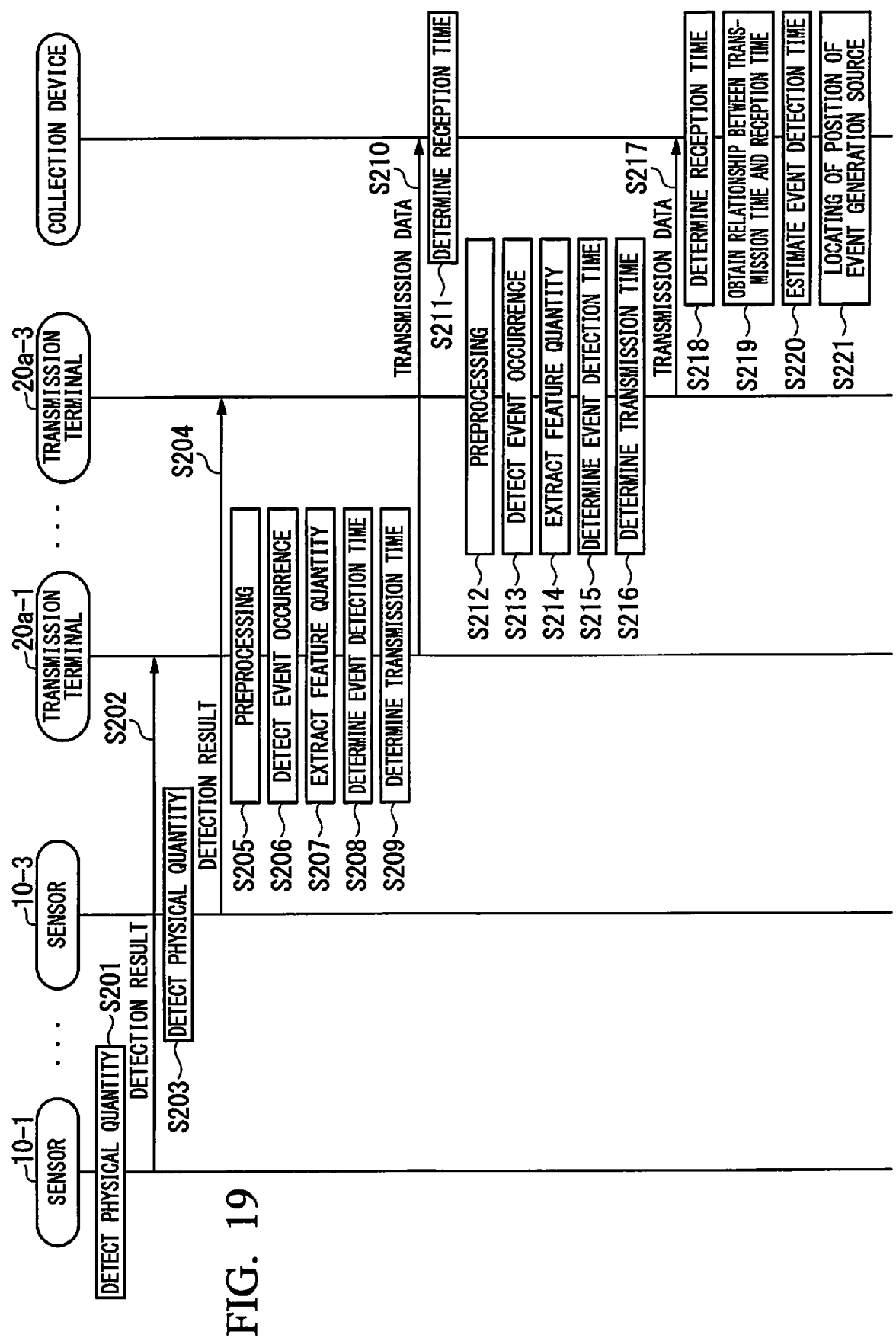
FIG. 19 is a sequence diagram showing a flow of a process performed by the sensor system according to the second embodiment.

FIG. 19 is a sequence diagram showing a flow of a process performed by the sensor system 100 according to the second embodiment. A case in which there are three sensors 10 (sensors 10-1 to 10-3), three transmission terminals 20*a* (transmission terminals 20*a*-1 to 20-3), and one collection device 30*a* will be described as an example with reference to FIG. 19. In FIG. 19, it is assumed that the sensor 10-1 is connected to the transmission terminal 20*a*-1, the sensor 10-2 is connected to the transmission terminal 20*a*-2, and the sensor 10-3 is connected to the transmission terminal 20*a*-3. Because the sensors 10-1 to 10-3 perform similar processes except that connection destinations are different, only the sensors 10-1 and 10-3 will be described with reference to FIG. 19. Because the transmission terminals 20*a*-1 to 20-3 perform similar processes except that connection destinations are different, only the transmission terminals 20*a*-1 and 20*a*-3 will be described with reference to FIG. 19.

The sensor 10-1 detects a physical quantity (step S201). The sensor 10-1 converts the detected physical quantity into an electrical signal. The sensor 10-1 transmits an electrical signal indicating the detection result to the transmission terminal 20a-1 (step S202).

The sensor 10-3 detects a physical quantity (step S203). The sensor 10-3 converts the detected physical quantity into an electrical signal. The sensor 10-3 transmits an electrical signal indicating the detection result to the transmission terminal 20a-3 (step S204).

The receiver 21-1 receives the electrical signal transmitted from the sensor 10-1. The transmission terminal 20a-1 performs preprocessing on the received electrical signal (step S205). The event signal generator 271a-1 detects the occurrence of an event on the basis of a preprocessed signal (step S206). The event signal generator 271a-1 outputs a first gate signal to the event time determiner 272a-1 and the feature quantity extraction unit 275-1. The feature quantity extraction unit 275-1 extracts a feature quantity from the preprocessed signal when the first gate signal output from the event signal generator 271a-1 has been input (step S207). The feature quantity extraction unit 275-1 outputs the extracted feature quantity to the detection signal generator 276-1.

The event time determiner 272a-1 determines a time at which the first gate signal has been input as the event detection time (step S208). The event time determiner 272a-1 outputs information of the determined event detection time to the detection signal generator 276-1. The event time determiner 272a-1 also outputs sensor data obtained from the sensor 10-1 to the detection signal generator 276-1. The detection signal generator 276-1 inputs the feature quantity output from the feature quantity extraction unit 275-1 and the event detection time and the sensor data output from the event time determiner 272a-1. The detection signal generator 276-1 generates detection information in which the feature quantity, the event detection time, and the sensor data are associated and outputs the generated detection information to the communicator 274a-1.

The communication time determiner 273a-1 inputs time information generated by the time information generator 26-1. The communication time determiner 273a-1 determines the transmission time on the basis of the input time information (step S209). The communication time determiner 273a-1 outputs information of the determined transmission time to the communicator 274a-1. The communicator 274a-1 generates transmission data including detection information output from the detection signal generator 276-1 and the transmission time output from the communication time determiner 273a-1. The communicator 274a-1 transmits the generated transmission data to the collection device 30a (step S210).

The communicator 33 of the collection device 30a receives the transmission data transmitted from the transmission terminal 20a-1. The communicator 33 outputs the received transmission data to the reception time determiner 34 and the time information processor 35. The reception time determiner 34 determines a reception time on the basis of the time information generated by the time information generator 32 and the transmission data output from the communicator 33 (step S211). Specifically, the reception time determiner 34 determines a time indicated by time information of a point in time at which the transmission data has been obtained as the reception time. The reception time determiner 34 outputs information of the determined reception time to the time information processor 35. The time information processor 35 saves the transmission data output from the communicator 33 and the information of the reception time output from the reception time determiner 34 in association in the storage unit for each sensor 10.

The receiver 21-3 receives an electrical signal transmitted from the sensor 10-3. The transmission terminal 20a-3 performs preprocessing on the received electrical signal (step S212). The event signal generator 271a-3 detects the occurrence of an event on the basis of a preprocessed signal (step S213). The event signal generator 271a-3 outputs a first gate signal to the event time determiner 272a-3 and the feature quantity extraction unit 275-3. The feature quantity extraction unit 275-3 extracts a feature quantity from the preprocessed signal when the first gate signal output from the event signal generator 271a-3 has been input (step S214). The feature quantity extraction unit 275-3 outputs the extracted feature quantity to the detection signal generator 276-3.

The event time determiner 272a-3 determines a time at which the first gate signal has been input as the event detection time (step S215). The event time determiner 272a-3 outputs information of the determined event detection time to the detection signal generator 276-3. Also, the event time determiner 272a-3 outputs sensor data obtained from the sensor 10-3 to the detection signal generator 276-3. The detection signal generator 276-3 inputs a feature quantity output from the feature quantity extraction unit 275-3 and the event detection time and sensor data output from the event time determiner 272a-3. The detection signal generator 276-3 generates detection information in which the feature quantity, the event detection time, and the sensor data are associated and outputs the generated detection information to the communicator 274a-3.

The communication time determiner 273a-3 inputs the time information generated by the time information generator 26-3. The communication time determiner 273a-3 determines a transmission time on the basis of the input time information (step S216). The communication time determiner 273a-3 outputs information of the determined transmission time to the communicator 274a-3. The communicator 274a-3 generates transmission data including detection information output from the detection signal generator 276-3 and the transmission time output from the communication time determiner 273a-3. The communicator 274a-3 transmits the generated transmission data to the collection device 30a (step S217).

The communicator 33 of the collection device 30a receives the transmission data transmitted from the transmission terminal 20a-3. The communicator 33 outputs the received transmission data to the reception time determiner 34 and the time information processor 35. The reception time determiner 34 determines a reception time on the basis of the time information generated by the time information generator 32 and the transmission data output from the communicator 33 (step S218). Specifically, the reception time determiner 34 determines a time indicated by the time information of a point in time at which the transmission data has been obtained as the reception time. The reception time determiner 34 outputs information of the determined reception time to the time information processor 35. The time information processor 35 saves the transmission data output from the communicator 33 and the reception time information output from the reception time determiner 34 in association in the storage unit for each sensor 10.

The processing of steps S201 to S218 is iteratively executed. When information of a plurality of transmission times and a plurality of reception times related to one sensor 10 are stored in the collection device 30a, the collection device 30a executes the processing of step S219. For example, in the case of FIG. 19, only the sensor 10-1 is connected to the transmission terminal 20a-1. Therefore, when information of a plurality of transmission times of transmission data from the transmission terminal 20a-1 and information of a plurality of reception times of transmission data in the collection device 30a are stored in the collection device 30a, the collection device 30a executes the processing of step S219.

The time information processor 35 obtains the relationship between the transmission time and the reception time for each sensor 10 on the basis of the information of the plurality of transmission times and the information of the plurality of reception times saved in the storage unit (step S219). Specifically, the time information processor 35 obtains the graph shown in FIG. 6 using the information of the plurality of transmission times and the information of the plurality of reception times. Subsequently, the time information processor 35 estimates the event detection time for each sensor 10 from the relationship between the transmission time and the reception time obtained from the obtained graph (step S220). The time information processor 35 outputs the event detection time and detection information to the position locator 36.

The position locator 36 locates a position of an elastic wave generation source on the basis of the event detection time and the detection information (step S221). Specifically, the position locator 36 first calculates a similarity of feature quantity information included in the detection information and divides a plurality of pieces of detection information into groups on the basis of whether or not the similarity of the feature quantity information is greater than or equal to a predetermined threshold value. Then, the position locator 36 recognizes the detection information included in the same group as detection information of the same generation source.

The similarity is determined by a distance between feature quantity information and feature quantity information. That is, the similarity increases as a distance between different pieces of feature quantity information decreases. The position locator 36 calculates a distance between pieces of feature quantity information according to a predetermined distance function. The distance function is a function for calculating, for example, a standard Euclidean distance, a Minkowski distance, a Mahalanobis distance, or the like. In particular, the Mahalanobis distance can be calculated in consideration of a correlation between pieces of feature quantity information and the group classification accuracy can be improved. Next, the position locator 36 calculates time difference information of the reception times of elastic waves between the plurality of sensors 10 by comparing estimated event detection times associated with feature quantity information (feature quantity information of detection information included in the same group) whose similarity is greater than or equal to a predetermined threshold value.

The position locator 36 identifies position information of the elastic wave generation source on the basis of the position information, the time difference information, and the propagation speed of elastic waves between the sensors 10.

Next, a method in which the position locator 36 identifies a position of the elastic wave generation source will be described with reference to FIGS. 20 and 21. For simplicity, a one-dimensional case will be described in detail. The principle is the same for the two-dimensional and three-dimensional cases.

By installing a plurality of sensors 10, the sensor system 100a can detect a difference between occurrence times of a plurality of events and can wirelessly locate a vibration generation source and a lightning generation position by a low-cost terminal. In such a system, because events occur at the same timing, event detection times between the plurality of sensors 10 are substantially the same time. Thus, a wireless collision can be prevented by waiting for a fixed random time after event detection.

Figure 20:
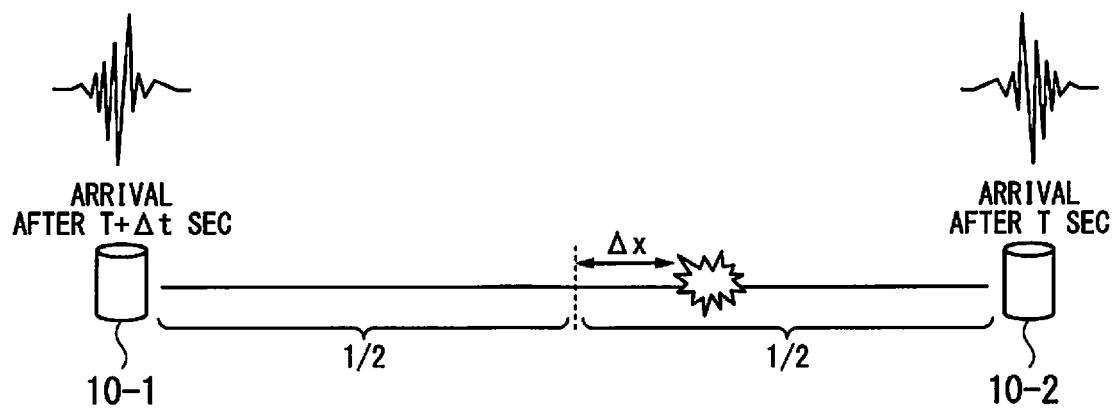
FIG. 20 is an explanatory diagram showing an example of a position identification method according to the second embodiment (a one-dimensional case).

FIG. 20 is an explanatory diagram showing an example of the position identification method according to the second embodiment (a one-dimensional case). A case in which a structure crack occurs between the sensors 10-1 and 10-2 and each of the sensors 10-1 and 10-2 detects elastic waves due to the crack will be described with reference to FIG. 20. A distance between the sensor 10-1 and the sensor 10-2 is assumed to be 1. A distance from an intermediate point between the sensor 10-1 and the sensor 10-2 to the crack is represented by $\Delta x$. At this time, when the sensor 10-2 detects elastic waves after T sec and the sensor 10-1 detects elastic waves after T+$\Delta t$ sec, $\Delta t$ can be represented by the following Eq. (3).

[Math. 3]

$$\Delta t = \frac{\left[\left[\frac{1}{2} + \Delta x\right] - \left[\frac{1}{2} - \Delta x\right]\right]}{v} = 2\Delta x / v \qquad \text{Eq. (3)}$$

Therefore, if the distance 1 and the elastic wave propagation velocity v are known, the position locator 36 can calculate a distance $\Delta x$ from an intermediate point between the sensor 10-1 and the sensor 10-2 to the crack on the basis of Eq. (3) by calculating a time difference information $\Delta t$. That is, the position locator 36 can identify the position information of the crack (the elastic wave generation source) from the time difference information $\Delta t$.

Next, the two-dimensional case will be briefly described.

Figure 21:
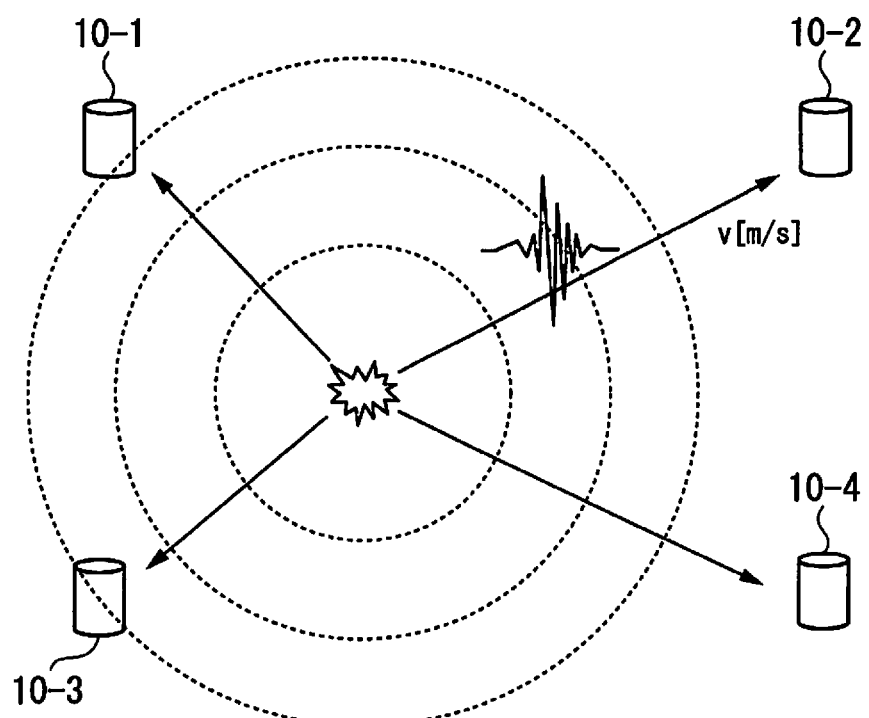
FIG. 21 is an explanatory diagram showing an example of a position identification method according to the second embodiment (a two-dimensional case).

FIG. 21 is an explanatory diagram showing an example of the position identification method according to the second embodiment (the two-dimensional case). An example in which a crack is generated in the structure and elastic waves due to the crack reach each of the sensors 10-1 to 10-4 at the propagation velocity v [m/s] is shown in FIG. 21. The time at which the elastic waves reach each of the sensors 10-1 to 10-4 differs according to each of the sensors 10-1 to 10-4.

When the time difference between the reception times of the elastic waves is known, it is possible to estimate that there are elastic wave generation sources on a circumference ARC_1 (radius $T_1$) around the sensor 10-1, a circumference ARC_2 (radius $T_2$) around the sensor 10-2, a circumference ARC_3 (radius $T_3$) around the sensor 10-3, and a circumference ARC_4 (radius $T_4$) around the sensor 10-4 as shown in FIG. 21. That is, the position locator 36 can identify an intersection of the circumferences ARC_1 to ARC_4 as position information of the elastic wave generation source.

Generally, the position of the elastic wave generation source can be identified using (number of dimensions+1) sensors 10. Therefore, in the three-dimensional case, it is possible to identify the position of the elastic wave generation source using the four sensors 10. Also, as the number of sensors 10 increases, the identification accuracy of the position information can increase.

According to the sensor system 100a configured as described above, it is possible to obtain an effect similar to that of the first embodiment.

In the sensor system 100a, an event detection time for each sensor 10 is estimated on the basis of information obtained from each sensor 10. Specifically, the collection device 30a estimates the event detection time according to correction that reduces the time error. Accordingly, because the collection device 30a locates a position of the event generation source on the basis of a corrected event detection time, the collection device 30a can locate the position with high accuracy.

Hereinafter, a modified example of the sensor system 100 according to the second embodiment will be described.

Some functions of the collection device 30a may be installed in the server device 50. For example, the time information processor 35 and the position locator 36 provided in the collection device 30a may be installed in the server device 50. In this case, the collection device 30a performs the data collection and the reception time determination and the server device 50 performs the event detection time estimation and the position location. Also, for example, the position locator 36 included in the collection device 30a may be installed in the server device 50. In this case, the collection device 30a performs the data collection, the reception time determination, and the event detection time estimation and the server device 50 performs the position location. When the server device 50 includes at least the time information processor 35, the server device 50 includes an acquisition unit that acquires all time information of an event detection time, a transmission time, and a reception time. Then, the time information processor 35 performs a process on the basis of a plurality of transmission times and a plurality of reception times that have been acquired. A specific process is as described above.

As described above, one of the collection device 30a and the server device 50 performs at least one of an event detection time estimation process and a position location process. The collection device 30a and the server device 50 are forms of a time information processing device.

Although a configuration in which the collection device 30a obtains a graph indicating a relationship between a transmission time and a reception time corresponding to the transmission time has been described in the present embodiment, the collection device 30a may be configured to calculate a time difference between transmission times and a time difference between reception times corresponding to the transmission times for each transmission terminal 20a and obtain a graph indicating a relationship between the calculated time difference between the transmission times and the calculated time difference between the reception times corresponding to the transmission times for each transmission terminal 20a. The position locator 36 of the collection device 30a locates the position of the event generation source using time difference information obtained for each transmission terminal 20a, position information of each transmission terminal 20a, and the propagation speed of elastic waves.

According to at least one embodiment described above, the event signal generator detects the occurrence of an event on the basis of the physical quantity detected by the sensor. The event time determiner determines an event detection time. The communication time determiner determines a transmission time at the time of transmission to the time information processing device. The communicator transmits time information of the transmission time and time information of the event detection time to the time information processing device. A reception time determiner determines a reception time of time information transmitted from the transmission terminal. When the time information processor performs a process based on a plurality of transmission times and a plurality of reception times, it is possible to minimize the deterioration in synchronization accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A sensor system comprising a plurality of sensors configured to detect a physical quantity, a plurality of transmission terminals connected to the plurality of sensors, and a time information processing device configured to perform a process based on information transmitted from the plurality of transmission terminals,
   wherein each of the plurality of transmission terminals comprises
   an event signal generator configured to detect the occurrence of an event on the basis of the physical quantity detected by each of the plurality of sensors connected to each of the plurality of transmission terminals;
   an event time determiner configured to determine a detection time of the event;
   a communication time determiner configured to determine a transmission time at the time of transmission to the time information processing device; and
   a communicator configured to transmit time information of the transmission time and time information of the detection time of the event to the time information processing device, and
   wherein the time information processing device comprises
   a reception time determiner configured to determine a reception time of the time information transmitted from the plurality of transmission terminals;
   a time information processor configured to perform a process based on a plurality of transmission times transmitted from each of the plurality of transmission terminals and a plurality of reception times; and
   a position locator configured to locate a generation source of the event,
   wherein the position locator locates the generation source of the event on the basis of the process result of the time information processor, position information of the plurality of sensors, and a propagation speed of the physical quantity.

2. The sensor system according to claim 1,
   wherein the time information processor obtains relationships between the plurality of transmission times and the plurality of reception times corresponding to the plurality of transmission times, and estimates the detection time of the event in the time information processing device using the obtained relationships and the detection time of the event.

3. The sensor system according to claim 1,
   wherein the time information processor estimates the detection time of the event for each of the plurality of transmission terminals, and
   wherein the position locator calculates time difference information of the event using the estimated detection time of the event for each transmission terminal, and locates the generation source of the event on the basis of the calculated time difference information, position information of the plurality of sensors and a propagation speed of the physical quantity detected by the plurality of sensors.

4. The sensor system according to claim 1, wherein the time information processor calculates a time difference between transmission times on the basis of the plurality of transmission times, and calculates a time difference between reception times on the basis of the plurality of reception times.

5. The sensor system according to claim 1, wherein the time information processor calculates a time difference between transmission times and a time difference between reception times for each of the plurality of transmission terminals, and
wherein the position locator locates the generation source of the event on the basis of the calculated time difference between the transmission times, the calculated time difference between the reception times, position information of the plurality of sensors and a propagation speed of the physical quantity detected by the plurality of sensors.

6. The sensor system according to claim 1, wherein, after the communicator transmits first transmission data including at least the detection time of the event and identification information for identifying its own transmission data to the time information processing device, the communicator transmits second transmission data including at least a transmission time of the first transmission data, identification information for identifying the first transmission data and identification information for identifying its own transmission data to the time information processing device.

7. The sensor system according to claim 1, wherein the communicator transmits second transmission data including at least a transmission time on the basis of an event that has virtually occurred to the time information processing device before and after transmission of first transmission data including at least the detection time of the event.

8. The sensor system according to claims 1, wherein the communicator transmits transmission data including at least the detection time of the event and the transmission time to the time information processing device at a timing when a random period of time has elapsed after detection of the occurrence of the event by the event signal generator.

9. A sensor system, comprising:
a transmission terminal comprising:
    an event signal generator configured to detect the occurrence of an event on the basis of a physical quantity detected by a sensor configured to detect the physical quantity;
    an event time determiner configured to determine a detection time of the event;
    a communication time determiner configured to determine a transmission time at the time of transmission; and
    a communicator configured to transmit time information of the transmission time and time information of the detection time of the event to another device,
    wherein the communicator transmits second transmission data including at least a transmission time on the basis of an event that has virtually occurred to another device before and after transmission of first transmission data including at least the detection time of the event; and
a time information processing device comprising:
    an acquisition unit configured to acquire time information of the detection time of the event, time information of a transmission time at which transmission data for providing a notification of the detection time of the event has been transmitted, and time information of a reception time of the transmission data;
    a time information processor configured to perform a process based on a plurality of transmission times and a plurality of reception times that have been acquired; and
    a position locator configured to locate a generation source of the event,
    wherein the position locator locates the generation source of the event on the basis of the process result of the time information processor, position information of a plurality of sensors configured to detect a physical quantity, and a propagation speed of the physical quantity.

10. A time information processing device comprising:
an acquisition unit configured to acquire time information of a detection time of an event, time information of a transmission time at which transmission data for providing a notification of the detection time of the event has been transmitted, and time information of a reception time of the transmission data;
a time information processor configured to perform a process based on a plurality of transmission times and a plurality of reception times that have been acquired; and
a position locator configured to locate a generation source of the event,
wherein the position locator locates the generation source of the event on the basis of the process result of the time information processor, position information of a plurality of sensors configured to detect a physical quantity, and a propagation speed of the physical quantity.

11. A synchronization method for use in a sensor system including a plurality of sensors configured to detect a physical quantity, a plurality of transmission terminals connected to the plurality of sensors, and a time information processing device configured to perform a process based on information transmitted from the plurality of transmission terminals, the synchronization method comprising:
detecting, by each of the plurality of transmission terminals, the occurrence of an event on the basis of the physical quantity detected by each of the plurality of sensors connected to each of the plurality of transmission terminals;
determining, by each of the plurality of transmission terminals, a detection time of the event;
determining, by each of the plurality of transmission terminals, a transmission time at the time of transmission to the time information processing device;
transmitting, by each of the plurality of transmission terminals, time information of the transmission time and time information of the detection time of the event to the time information processing device;
determining, by the time information processing device, a reception time of the time information transmitted from the plurality of transmission terminals;
performing, by the time information processing device, a process based on a plurality of transmission times transmitted from each of the plurality of transmission terminals and a plurality of reception times; and locating, by the time information processing device, the generation source of the event on the basis of the process result of the time information processor, position information of the plurality of sensors and a propagation speed of the physical quantity.

\* \* \* \* \*

UNITED STATES PATENT AND TRADEMARK OFFICE
CERTIFICATE OF CORRECTION

PATENT NO. : 11,329,744 B2
APPLICATION NO. : 16/810126
DATED : May 10, 2022
INVENTOR(S) : Yuki Ueda It is certified that error appears in the above-identified patent and that said Letters Patent is hereby corrected as shown below:

In the Claims

In Claim 8, Column 25, Line 44, "according to claims 1," should read --according to claim 1,--.

Signed and Sealed this
First Day of November, 2022

Katherine Kelly Vidal
Director of the United States Patent and Trademark Office